US009468364B2

(12) United States Patent
Malchano et al.

(10) Patent No.: US 9,468,364 B2
(45) Date of Patent: Oct. 18, 2016

(54) INTRAVASCULAR CATHETER WITH HOOD AND IMAGE PROCESSING SYSTEMS

(75) Inventors: Zachary J. Malchano, San Francisco, CA (US); Ruey-Feng Peh, Mountain View, CA (US); Vahid Saadat, Atherton, CA (US); Ted J. Cooper, Sunnyvale, CA (US); David Miller, Cupertino, CA (US); Veerappan Swaminathan, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 960 days.

(21) Appl. No.: 12/618,306

(22) Filed: Nov. 13, 2009

(65) Prior Publication Data

US 2010/0130836 A1 May 27, 2010

Related U.S. Application Data

(60) Provisional application No. 61/114,834, filed on Nov. 14, 2008.

(51) Int. Cl.
*A61B 5/00* (2006.01)
*A61B 1/05* (2006.01)
*A61B 5/042* (2006.01)
*A61B 5/0472* (2006.01)
*A61B 5/113* (2006.01)
*A61B 18/14* (2006.01)

(52) U.S. Cl.
CPC .............. *A61B 1/05* (2013.01); *A61B 5/042* (2013.01); *A61B 5/0472* (2013.01); *A61B 5/113* (2013.01); *A61B 5/7285* (2013.01); *A61B 5/7289* (2013.01); *A61B 18/1492* (2013.01); *A61B 2218/002* (2013.01)

(58) Field of Classification Search
CPC ............................ A61B 1/05; A61B 5/7285
USPC ......... 358/516; 600/104, 109, 112, 114, 118, 600/121, 301, 407, 425, 459, 463, 476, 600/478; 604/523, 528; 606/14, 41, 192; 607/122
See application file for complete search history.

(56) References Cited

U.S. PATENT DOCUMENTS 623,022 A 4/1899 Johnson
2,305,462 A 12/1942 Wolf
(Continued)

FOREIGN PATENT DOCUMENTS

DE 10028155 A1 12/2000
EP 0283661 9/1988
(Continued)

OTHER PUBLICATIONS

Saliba et al, Intracardiac echocardiography during catheter ablation of atrial fibrillation, Europace 2008, 10,i42-47.*
(Continued)

*Primary Examiner* — Serkan Akar

(57) ABSTRACT

Image processing systems are described which utilize various methods and processing algorithms for enhancing or facilitating visual detection and/or sensing modalities for images captured in vivo by an intravascular visualization and treatment catheter. Such assemblies are configured to deliver energy, such as RF ablation, to an underlying target tissue for treatment in a controlled manner while directly visualizing the tissue during the ablation process.

8 Claims, 24 Drawing Sheets

(56) References Cited

U.S. PATENT DOCUMENTS

| | | | |
|---|---|---|---|
| 2,574,840 A | 11/1951 | Pieri et al. | |
| 2,688,329 A | 9/1954 | Wallace | |
| 3,162,190 A | 12/1964 | Gizzo | |
| 3,452,740 A | 7/1969 | Muller | |
| 3,866,599 A | 2/1975 | Johnson | |
| 3,874,388 A | 4/1975 | King et al. | |
| 3,974,834 A | 8/1976 | Kane | |
| 4,033,331 A | 7/1977 | Guss et al. | |
| 4,175,545 A | 11/1979 | Termanini | |
| 4,224,929 A | 9/1980 | Furihata | |
| 4,326,529 A | 4/1982 | Doss et al. | |
| 4,445,892 A | 5/1984 | Hussein et al. | |
| 4,470,407 A | 9/1984 | Hussein et al. | |
| 4,569,335 A | 2/1986 | Tsuno | |
| 4,576,146 A | 3/1986 | Kawazoe et al. | |
| 4,615,333 A | 10/1986 | Taguchi | |
| 4,619,247 A | 10/1986 | Inoue et al. | |
| 4,676,258 A | 6/1987 | Inokuchi et al. | |
| 4,681,093 A | 7/1987 | Ono et al. | |
| 4,689,041 A | 8/1987 | Corday et al. | |
| 4,709,698 A | 12/1987 | Johnston et al. | |
| 4,710,192 A | 12/1987 | Liotta et al. | |
| 4,717,387 A | 1/1988 | Inoue et al. | |
| 4,723,936 A | 2/1988 | Buchbinder et al. | |
| 4,727,418 A | 2/1988 | Kato et al. | |
| 4,779,611 A | 10/1988 | Grooters et al. | |
| 4,781,681 A | 11/1988 | Sharrow et al. | |
| 4,784,133 A | 11/1988 | Mackin | |
| 4,800,876 A | 1/1989 | Fox et al. | |
| 4,848,323 A | 7/1989 | Marijnissen et al. | |
| 4,898,577 A | 2/1990 | Badger et al. | |
| 4,911,148 A | 3/1990 | Sosnowski et al. | |
| 4,914,521 A | 4/1990 | Adair | |
| 4,943,290 A | 7/1990 | Rexroth et al. | |
| 4,950,285 A | 8/1990 | Wilk | |
| 4,957,484 A | 9/1990 | Murtfeldt | |
| 4,960,411 A | 10/1990 | Buchbinder | |
| 4,961,738 A | 10/1990 | Mackin | |
| 4,976,710 A | 12/1990 | Mackin | |
| 4,991,578 A | 2/1991 | Cohen | |
| 4,994,069 A | 2/1991 | Ritchart et al. | |
| 4,998,916 A | 3/1991 | Hammerslag et al. | |
| 4,998,972 A | 3/1991 | Chin et al. | |
| 5,029,574 A | 7/1991 | Shimamura et al. | |
| 5,057,106 A | 10/1991 | Kasevich et al. | |
| 5,090,959 A | 2/1992 | Samson et al. | |
| 5,114,414 A | 5/1992 | Buchbinder | |
| 5,116,317 A | 5/1992 | Carson, Jr. et al. | |
| 5,123,428 A | 6/1992 | Schwarz | |
| 5,125,895 A | 6/1992 | Buchbinder et al. | |
| RE34,002 E | 7/1992 | Adair | |
| 5,171,259 A | 12/1992 | Inoue | |
| 5,188,596 A | 2/1993 | Condon et al. | |
| 5,190,528 A | 3/1993 | Fonger et al. | |
| 5,203,772 A | 4/1993 | Hammerslag et al. | |
| 5,246,420 A | 9/1993 | Kraus et al. | |
| 5,254,088 A | 10/1993 | Lundquist et al. | |
| 5,271,383 A | 12/1993 | Wilk | |
| 5,273,535 A | 12/1993 | Edwards et al. | |
| 5,281,238 A | 1/1994 | Chin et al. | |
| 5,282,827 A | 2/1994 | Kensey et al. | |
| 5,306,234 A | 4/1994 | Johnson | |
| 5,313,943 A | 5/1994 | Houser et al. | |
| 5,318,525 A | 6/1994 | West et al. | |
| 5,330,496 A | 7/1994 | Alferness | |
| 5,334,159 A | 8/1994 | Turkel | |
| 5,334,193 A | 8/1994 | Nardella | |
| 5,336,252 A | 8/1994 | Cohen | |
| 5,339,800 A | 8/1994 | Wiita et al. | |
| 5,346,504 A | 9/1994 | Ortiz et al. | |
| 5,348,554 A | 9/1994 | Imran et al. | |
| 5,353,792 A | 10/1994 | Lubbers et al. | |
| 5,358,478 A | 10/1994 | Thompson et al. | |
| 5,358,479 A | 10/1994 | Wilson | |
| 5,370,647 A | 12/1994 | Graber et al. | |
| 5,373,840 A | 12/1994 | Knighton | |
| 5,375,612 A | 12/1994 | Cottenceau et al. | |
| 5,385,148 A | 1/1995 | Lesh et al. | |
| 5,389,073 A | 2/1995 | Imran | |
| 5,391,147 A | 2/1995 | Imran et al. | |
| 5,403,326 A | 4/1995 | Harrison et al. | |
| 5,405,376 A | 4/1995 | Mulier et al. | |
| 5,409,469 A | 4/1995 | Schaerf | |
| 5,409,483 A | 4/1995 | Campbell et al. | |
| 5,421,338 A | 6/1995 | Crowley et al. | |
| 5,431,649 A | 7/1995 | Mulier et al. | |
| 5,447,497 A | 9/1995 | Sogard et al. | |
| 5,453,785 A | 9/1995 | Lenhardt et al. | |
| 5,462,521 A | 10/1995 | Brucker et al. | |
| 5,464,395 A | 11/1995 | Faxon et al. | |
| 5,471,515 A | 11/1995 | Fossum et al. | |
| 5,489,270 A | 2/1996 | van Erp | |
| 5,498,230 A | 3/1996 | Adair | |
| 5,498,239 A | 3/1996 | Galel et al. | |
| 5,505,730 A | 4/1996 | Edwards | |
| 5,515,853 A | 5/1996 | Smith et al. | |
| 5,527,338 A | 6/1996 | Purdy | |
| 5,549,603 A | 8/1996 | Feiring | |
| 5,558,619 A | 9/1996 | Kami et al. | |
| 5,571,088 A | 11/1996 | Lennox et al. | |
| 5,575,756 A | 11/1996 | Karasawa et al. | |
| 5,575,810 A | 11/1996 | Swanson et al. | |
| 5,584,872 A | 12/1996 | LaFontaine et al. | |
| 5,588,432 A | 12/1996 | Crowley | |
| 5,591,119 A | 1/1997 | Adair | |
| 5,593,405 A | 1/1997 | Osypka | |
| 5,593,422 A | 1/1997 | Muijs Van de Moer et al. | |
| 5,593,424 A | 1/1997 | Northrup, III | |
| 5,611,777 A | 3/1997 | Bowden et al. | |
| 5,672,153 A | 9/1997 | Lax et al. | |
| 5,676,693 A | 10/1997 | LaFontaine | |
| 5,681,308 A | 10/1997 | Edwards et al. | |
| 5,695,448 A | 12/1997 | Kimura et al. | |
| 5,697,281 A | 12/1997 | Eggers et al. | |
| 5,697,882 A | 12/1997 | Eggers et al. | |
| 5,709,224 A | 1/1998 | Behl et al. | |
| 5,713,867 A | 2/1998 | Morris | |
| 5,713,907 A | 2/1998 | Hogendijk et al. | |
| 5,713,946 A | 2/1998 | Ben-Haim | |
| 5,716,321 A | 2/1998 | Kerin et al. | |
| 5,722,403 A | 3/1998 | McGee et al. | |
| 5,725,523 A | 3/1998 | Mueller | |
| 5,738,649 A | 4/1998 | Macoviak | |
| 5,741,320 A | 4/1998 | Thornton et al. | |
| 5,746,747 A | 5/1998 | McKeating | |
| 5,749,846 A | 5/1998 | Edwards et al. | |
| 5,749,890 A | 5/1998 | Shaknovich | |
| 5,752,518 A | 5/1998 | McGee et al. | |
| 5,754,313 A | 5/1998 | Pelchy et al. | |
| 5,762,604 A | 6/1998 | Kieturakis | |
| 5,766,137 A | 6/1998 | Omata | |
| 5,769,846 A | 6/1998 | Edwards et al. | |
| 5,792,045 A | 8/1998 | Adair | |
| 5,797,903 A | 8/1998 | Swanson et al. | |
| 5,824,005 A | 10/1998 | Motamedi et al. | |
| 5,827,268 A | 10/1998 | Laufer | |
| 5,829,447 A | 11/1998 | Stevens et al. | |
| 5,843,118 A | 12/1998 | Sepetka et al. | |
| 5,848,969 A | 12/1998 | Panescu et al. | |
| 5,857,760 A | 1/1999 | Giba et al. | |
| 5,860,974 A | 1/1999 | Abele | |
| 5,860,991 A | 1/1999 | Klein et al. | |
| 5,865,791 A | 2/1999 | Whayne et al. | |
| 5,873,815 A | 2/1999 | Kerin et al. | |
| 5,876,373 A | 3/1999 | Giba et al. | |
| 5,876,426 A | 3/1999 | Kume et al. | |
| 5,879,366 A | 3/1999 | Shaw et al. | |
| 5,895,417 A | 4/1999 | Pomeranz et al. | |
| 5,897,487 A | 4/1999 | Ouchi | |
| 5,897,553 A | 4/1999 | Mulier et al. | |
| 5,902,328 A | 5/1999 | LaFontaine et al. | |
| 5,904,651 A * | 5/1999 | Swanson et al. | 600/407 |
| 5,908,445 A * | 6/1999 | Whayne et al. | 607/122 |
| 5,928,250 A | 7/1999 | Koike et al. | |

(56) References Cited

U.S. PATENT DOCUMENTS

| | | | |
|---|---|---|---|
| 5,929,901 A | 7/1999 | Adair et al. | |
| 5,935,102 A | 8/1999 | Bowden et al. | |
| 5,938,586 A | 8/1999 | Wilk et al. | |
| 5,941,845 A | 8/1999 | Tu et al. | |
| 5,944,690 A | 8/1999 | Falwell et al. | |
| 5,964,755 A | 10/1999 | Edwards | |
| 5,968,010 A | 10/1999 | Waxman et al. | |
| 5,968,053 A | 10/1999 | Revelas | |
| 5,971,983 A | 10/1999 | Lesh | |
| 5,985,307 A | 11/1999 | Hanson et al. | |
| 5,986,693 A | 11/1999 | Adair et al. | |
| 5,997,571 A | 12/1999 | Farr et al. | |
| 6,004,269 A | 12/1999 | Crowley et al. | |
| 6,012,457 A | 1/2000 | Lesh | |
| 6,024,740 A | 2/2000 | Lesh et al. | |
| 6,027,501 A | 2/2000 | Goble et al. | |
| 6,028,622 A | 2/2000 | Suzuki | |
| 6,035,224 A | 3/2000 | Tockman | |
| 6,036,685 A | 3/2000 | Mueller | |
| 6,043,839 A | 3/2000 | Adair et al. | |
| 6,047,218 A * | 4/2000 | Whayne et al. | 607/122 |
| 6,063,077 A | 5/2000 | Schaer | |
| 6,063,081 A | 5/2000 | Mulier et al. | |
| 6,068,653 A | 5/2000 | LaFontaine | |
| 6,071,302 A | 6/2000 | Sinofsky et al. | |
| 6,081,740 A | 6/2000 | Gombrich et al. | |
| 6,086,528 A | 7/2000 | Adair | |
| 6,086,534 A | 7/2000 | Kesten | |
| 6,086,557 A | 7/2000 | Morejohn et al. | |
| 6,099,498 A | 8/2000 | Addis | |
| 6,099,514 A | 8/2000 | Sharkey et al. | |
| 6,102,905 A | 8/2000 | Baxter et al. | |
| 6,110,145 A | 8/2000 | Macoviak | |
| 6,112,123 A | 8/2000 | Kelleher et al. | |
| 6,115,626 A | 9/2000 | Whayne et al. | |
| 6,122,552 A | 9/2000 | Tockman | |
| 6,123,703 A | 9/2000 | Tu et al. | |
| 6,123,718 A | 9/2000 | Tu et al. | |
| 6,129,724 A | 10/2000 | Fleischman et al. | |
| 6,139,508 A | 10/2000 | Simpson et al. | |
| 6,142,993 A | 11/2000 | Whayne et al. | |
| 6,152,144 A | 11/2000 | Lesh et al. | |
| 6,156,350 A | 12/2000 | Constantz | |
| 6,159,203 A | 12/2000 | Sinofsky | |
| 6,161,543 A | 12/2000 | Cox et al. | |
| 6,164,283 A | 12/2000 | Lesh | |
| 6,167,297 A | 12/2000 | Benaron | |
| 6,168,591 B1 | 1/2001 | Sinofsky | |
| 6,168,594 B1 | 1/2001 | LaFontaine et al. | |
| 6,174,307 B1 | 1/2001 | Daniel et al. | |
| 6,178,346 B1 | 1/2001 | Amundson et al. | |
| 6,190,381 B1 | 2/2001 | Olsen et al. | |
| 6,210,407 B1 | 4/2001 | Webster | |
| 6,211,904 B1 | 4/2001 | Adair et al. | |
| 6,224,553 B1 | 5/2001 | Nevo | |
| 6,231,561 B1 | 5/2001 | Frazier et al. | |
| 6,235,044 B1 | 5/2001 | Root et al. | |
| 6,237,605 B1 | 5/2001 | Vaska et al. | |
| 6,238,393 B1 | 5/2001 | Mulier et al. | |
| 6,240,312 B1 | 5/2001 | Alfano et al. | |
| 6,254,598 B1 | 7/2001 | Edwards et al. | |
| 6,258,083 B1 | 7/2001 | Daniel et al. | |
| 6,270,492 B1 | 8/2001 | Sinofsky | |
| 6,275,255 B1 | 8/2001 | Adair et al. | |
| 6,277,064 B1 | 8/2001 | Yoon | |
| 6,283,951 B1 | 9/2001 | Flaherty et al. | |
| 6,290,689 B1 | 9/2001 | Delaney et al. | |
| 6,306,081 B1 | 10/2001 | Ishikawa et al. | |
| 6,310,642 B1 | 10/2001 | Adair et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,315,777 B1 | 11/2001 | Comben | |
| 6,315,778 B1 | 11/2001 | Gambale et al. | |
| 6,322,536 B1 | 11/2001 | Rosengart et al. | |
| 6,325,797 B1 | 12/2001 | Stewart et al. | |
| 6,328,727 B1 | 12/2001 | Frazier et al. | |
| 6,358,247 B1 | 3/2002 | Altman et al. | |
| 6,358,248 B1 | 3/2002 | Mulier et al. | |
| 6,375,654 B1 | 4/2002 | McIntyre | |
| 6,379,345 B1 | 4/2002 | Constantz | |
| 6,385,476 B1 | 5/2002 | Osadchy et al. | |
| 6,387,043 B1 | 5/2002 | Yoon | |
| 6,387,071 B1 | 5/2002 | Constantz | |
| 6,394,096 B1 | 5/2002 | Constantz | |
| 6,396,873 B1 | 5/2002 | Goldstein et al. | |
| 6,398,780 B1 | 6/2002 | Farley et al. | |
| 6,401,719 B1 | 6/2002 | Farley et al. | |
| 6,409,722 B1 | 6/2002 | Hoey et al. | |
| 6,416,511 B1 | 7/2002 | Lesh et al. | |
| 6,419,669 B1 | 7/2002 | Frazier et al. | |
| 6,423,051 B1 | 7/2002 | Kaplan et al. | |
| 6,423,055 B1 | 7/2002 | Farr et al. | |
| 6,423,058 B1 | 7/2002 | Edwards et al. | |
| 6,428,536 B2 | 8/2002 | Panescu et al. | |
| 6,440,119 B1 | 8/2002 | Nakada et al. | |
| 6,458,107 B1 | 10/2002 | Ockuly | |
| 6,458,151 B1 | 10/2002 | Saltiel | |
| 6,464,631 B1 | 10/2002 | Girke et al. | |
| 6,464,697 B1 | 10/2002 | Edwards et al. | |
| 6,474,340 B1 | 11/2002 | Vaska et al. | |
| 6,475,223 B1 | 11/2002 | Werp et al. | |
| 6,478,769 B1 | 11/2002 | Parker | |
| 6,482,162 B1 | 11/2002 | Moore | |
| 6,484,727 B1 | 11/2002 | Vaska et al. | |
| 6,485,489 B2 | 11/2002 | Teirstein et al. | |
| 6,488,671 B1 | 12/2002 | Constantz et al. | |
| 6,494,902 B2 | 12/2002 | Hoey et al. | |
| 6,497,705 B2 | 12/2002 | Comben | |
| 6,500,174 B1 | 12/2002 | Maguire et al. | |
| 6,502,576 B1 | 1/2003 | Lesh | |
| 6,514,249 B1 | 2/2003 | Maguire et al. | |
| 6,517,533 B1 | 2/2003 | Swaminathan | |
| 6,527,979 B2 | 3/2003 | Constantz et al. | |
| 6,532,380 B1 | 3/2003 | Close et al. | |
| 6,533,767 B2 | 3/2003 | Johansson et al. | |
| 6,537,272 B2 | 3/2003 | Christopherson et al. | |
| 6,540,733 B2 | 4/2003 | Constantz et al. | |
| 6,540,744 B2 | 4/2003 | Hassett et al. | |
| 6,544,195 B2 | 4/2003 | Wilson et al. | |
| 6,547,780 B1 | 4/2003 | Sinofsky | |
| 6,558,375 B1 | 5/2003 | Sinofsky et al. | |
| 6,562,020 B1 | 5/2003 | Constantz et al. | |
| 6,562,049 B1 | 5/2003 | Norlander et al. | |
| 6,572,609 B1 | 6/2003 | Farr et al. | |
| 6,579,278 B1 | 6/2003 | Bencini | |
| 6,579,285 B2 | 6/2003 | Sinofsky | |
| 6,585,718 B2 | 7/2003 | Hayzelden et al. | |
| 6,585,732 B2 | 7/2003 | Mulier et al. | |
| 6,587,709 B2 | 7/2003 | Solf et al. | |
| 6,592,581 B2 | 7/2003 | Belson et al. | |
| 6,593,884 B2 | 7/2003 | Gilboa et al. | |
| 6,605,055 B1 | 8/2003 | Sinofsky et al. | |
| 6,610,007 B2 | 8/2003 | Belson et al. | |
| 6,613,062 B1 | 9/2003 | Leckrone et al. | |
| 6,616,628 B2 | 9/2003 | Hayzelden | |
| 6,622,732 B2 | 9/2003 | Constantz | |
| 6,626,855 B1 | 9/2003 | Weng et al. | |
| 6,626,900 B1 | 9/2003 | Sinofsky et al. | |
| 6,635,070 B2 | 10/2003 | Leeflang et al. | |
| 6,638,268 B2 | 10/2003 | Niazi | |
| 6,645,202 B1 | 11/2003 | Pless et al. | |
| 6,650,923 B1 | 11/2003 | Lesh et al. | |
| 6,658,279 B2 * | 12/2003 | Swanson et al. | 600/407 |
| 6,659,940 B2 | 12/2003 | Adler | |
| 6,673,090 B2 | 1/2004 | Root et al. | |
| 6,676,656 B2 | 1/2004 | Sinofsky | |
| 6,679,836 B2 | 1/2004 | Couvillon, Jr. | |
| 6,682,526 B1 | 1/2004 | Jones et al. | |
| 6,689,128 B2 | 2/2004 | Sliwa, Jr. et al. | |
| 6,692,430 B2 | 2/2004 | Adler | |
| 6,701,581 B2 | 3/2004 | Senovich et al. | |
| 6,701,931 B2 | 3/2004 | Sliwa, Jr. et al. | |
| 6,702,780 B1 | 3/2004 | Gilboa et al. | |

(56) References Cited

U.S. PATENT DOCUMENTS

| | | |
|---|---|---|
| 6,704,043 B2 | 3/2004 | Goldstein et al. |
| 6,706,039 B2 | 3/2004 | Mulier et al. |
| 6,712,798 B2 | 3/2004 | Constantz |
| 6,719,747 B2 | 4/2004 | Constantz et al. |
| 6,719,755 B2 | 4/2004 | Sliwa, Jr. et al. |
| 6,730,058 B2 | 5/2004 | Hayzelden |
| 6,730,063 B2 | 5/2004 | Delaney et al. |
| 6,736,810 B2 | 5/2004 | Hoey et al. |
| 6,743,227 B2 | 6/2004 | Seraj et al. |
| 6,751,492 B2 | 6/2004 | Ben-Haim |
| 6,755,790 B2 | 6/2004 | Stewart et al. |
| 6,755,811 B1 | 6/2004 | Constantz |
| 6,755,812 B2 | 6/2004 | Peterson et al. |
| 6,764,487 B2 | 7/2004 | Mulier et al. |
| 6,771,996 B2 | 8/2004 | Bowe et al. |
| 6,773,402 B2 | 8/2004 | Govari et al. |
| 6,780,151 B2 | 8/2004 | Grabover et al. |
| 6,783,510 B1 | 8/2004 | Gibson et al. |
| 6,800,056 B2 | 10/2004 | Tartaglia et al. |
| 6,805,128 B1 | 10/2004 | Pless et al. |
| 6,805,129 B1 | 10/2004 | Pless et al. |
| 6,811,562 B1 | 11/2004 | Pless |
| 6,833,814 B2 | 12/2004 | Gilboa et al. |
| 6,840,923 B1 | 1/2005 | Lapcevic |
| 6,840,936 B2 | 1/2005 | Sliwa, Jr. et al. |
| 6,849,073 B2 | 2/2005 | Hoey et al. |
| 6,858,005 B2 | 2/2005 | Ohline et al. |
| 6,858,026 B2 | 2/2005 | Sliwa, Jr. et al. |
| 6,863,668 B2 | 3/2005 | Gillespie et al. |
| 6,866,651 B2 | 3/2005 | Constantz |
| 6,887,237 B2 | 5/2005 | McGaffigan |
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,286 B2 | 7/2005 | Kazakevich |
| 6,923,805 B1 | 8/2005 | LaFontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa, Jr. et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton, IV et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,191,015 B2 | 3/2007 | Lamson et al. |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,398,781 B1 | 7/2008 | Chin |
| 7,435,248 B2 | 10/2008 | Taimisto et al. |
| 7,527,625 B2 | 5/2009 | Knight et al. |
| 7,534,204 B2 | 5/2009 | Starksen et al. |
| 7,569,052 B2 | 8/2009 | Phan et al. |
| 7,610,104 B2 | 10/2009 | Kaplan et al. |
| 7,736,347 B2 | 6/2010 | Kaplan et al. |
| 7,758,499 B2 | 7/2010 | Adler |
| 7,860,555 B2 * | 12/2010 | Saadat ............ 600/476 |
| 7,860,556 B2 | 12/2010 | Saadat |
| 1,060,665 A1 | 5/2013 | Bell |
| 2001/0005789 A1 | 6/2001 | Root et al. |
| 2001/0007937 A1 | 7/2001 | MacKin |
| 2001/0020126 A1* | 9/2001 | Swanson et al. ............ 600/407 |
| 2001/0031912 A1 | 10/2001 | Adler |
| 2001/0039416 A1 | 11/2001 | Moorman et al. |
| 2001/0047136 A1 | 11/2001 | Domanik et al. |
| 2001/0047184 A1 | 11/2001 | Connors |
| 2001/0052930 A1 | 12/2001 | Adair et al. |
| 2002/0004644 A1 | 1/2002 | Koblish |
| 2002/0026145 A1 | 2/2002 | Bagaoisan et al. |
| 2002/0065455 A1 | 5/2002 | Ben-Haim et al. |
| 2002/0065512 A1 | 5/2002 | Fjield et al. |
| 2002/0068853 A1 | 6/2002 | Adler et al. |
| 2002/0080248 A1 | 6/2002 | Adair et al. |
| 2002/0087166 A1 | 7/2002 | Brock et al. |
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0165598 A1 | 11/2002 | Wahr et al. |
| 2002/0169377 A1 | 11/2002 | Khairkhahan et al. |
| 2003/0035156 A1* | 2/2003 | Cooper ............ 358/516 |
| 2003/0069593 A1 | 4/2003 | Tremulis et al. |
| 2003/0092995 A1 | 5/2003 | Thompson |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0216720 A1 | 11/2003 | Sinofsky et al. |
| 2003/0220574 A1 | 11/2003 | Markus et al. |
| 2003/0222325 A1 | 12/2003 | Jacobsen et al. |
| 2003/0233115 A1 | 12/2003 | Eversull et al. |
| 2004/0006333 A1 | 1/2004 | Arnold et al. |
| 2004/0009155 A1 | 1/2004 | Palasis et al. |
| 2004/0015193 A1 | 1/2004 | Lamson et al. |
| 2004/0039371 A1 | 2/2004 | Tockman et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0054724 A1 | 3/2004 | Sudo |
| 2004/0082833 A1 | 4/2004 | Adler |
| 2004/0097788 A1 | 5/2004 | Mourlas et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0210278 A1 | 10/2004 | Boll et al. |
| 2004/0215183 A1 | 10/2004 | Hoey et al. |
| 2004/0220470 A1 | 11/2004 | Karmarkar et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |

(56) References Cited

U.S. PATENT DOCUMENTS

| | | |
|---|---|---|
| 2005/0027243 A1 | 2/2005 | Gibson et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0085842 A1 | 4/2005 | Eversull |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1 | 6/2005 | Starksen et al. |
| 2005/0124969 A1 | 6/2005 | Fitzgerald et al. |
| 2005/0131401 A1 | 6/2005 | Malecki et al. |
| 2005/0149105 A1 | 7/2005 | Leeflang |
| 2005/0154252 A1 | 7/2005 | Sharkey et al. |
| 2005/0158899 A1 | 7/2005 | Jacobsen et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0182465 A1 | 8/2005 | Ness |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0267452 A1 | 12/2005 | Farr et al. |
| 2006/0009715 A1 | 1/2006 | Khairkhahan et al. |
| 2006/0009737 A1 | 1/2006 | Whiting et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0030844 A1* | 2/2006 | Knight et al. .................. 606/41 |
| 2006/0069303 A1 | 3/2006 | Couvillon et al. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0184048 A1* | 8/2006 | Saadat .................. 600/478 |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0258909 A1* | 11/2006 | Saadat et al. .................. 600/121 |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1* | 3/2007 | Webler .................. 600/425 |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100241 A1 | 5/2007 | Adler |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1* | 7/2007 | Webler et al. .................. 600/459 |
| 2007/0167828 A1* | 7/2007 | Saadat .................. 600/463 |
| 2007/0265609 A1 | 11/2007 | Thapliyal et al. |
| 2007/0265610 A1 | 11/2007 | Thapliyal et al. |
| 2007/0270642 A1* | 11/2007 | Bayer et al. .................. 600/109 |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033290 A1 | 2/2008 | Saadat et al. |
| 2008/0057106 A1 | 3/2008 | Erickson et al. |
| 2008/0058590 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0214889 A1 | 9/2008 | Saadat et al. |
| 2008/0228032 A1 | 9/2008 | Starksen et al. |
| 2008/0275300 A1 | 11/2008 | Rothe et al. |
| 2008/0281293 A1* | 11/2008 | Peh et al. .................. 604/523 |
| 2008/0287790 A1 | 11/2008 | Li |
| 2008/0287805 A1 | 11/2008 | Li |
| 2009/0030276 A1* | 1/2009 | Saadat et al. .................. 600/112 |
| 2009/0030412 A1* | 1/2009 | Willis et al. .................. 606/41 |
| 2009/0054803 A1 | 2/2009 | Saadat et al. |
| 2009/0062790 A1* | 3/2009 | Malchano et al. .................. 606/41 |
| 2009/0076489 A1 | 3/2009 | Welches et al. |
| 2009/0076498 A1* | 3/2009 | Saadat et al. .................. 606/41 |
| 2009/0082623 A1* | 3/2009 | Rothe et al. .................. 600/109 |
| 2009/0125022 A1* | 5/2009 | Saadat et al. .................. 606/41 |
| 2009/0143640 A1* | 6/2009 | Saadat et al. .................. 600/104 |
| 2009/0187074 A1* | 7/2009 | Saadat et al. .................. 600/114 |
| 2009/0203962 A1* | 8/2009 | Miller et al. .................. 600/109 |
| 2009/0221871 A1* | 9/2009 | Peh et al. .................. 600/118 |
| 2009/0227999 A1* | 9/2009 | Willis et al. .................. 606/14 |
| 2009/0264727 A1 | 10/2009 | Markowitz et al. |
| 2009/0267773 A1 | 10/2009 | Markowitz et al. |
| 2009/0275799 A1* | 11/2009 | Saadat et al. .................. 600/109 |
| 2009/0275842 A1* | 11/2009 | Saadat et al. .................. 600/478 |
| 2009/0299363 A1* | 12/2009 | Saadat et al. .................. 606/41 |
| 2009/0326572 A1* | 12/2009 | Peh et al. .................. 606/192 |
| 2010/0004506 A1* | 1/2010 | Saadat .................. 600/109 |
| 2010/0004633 A1* | 1/2010 | Rothe et al. .................. 604/528 |
| 2010/0004661 A1 | 1/2010 | Verin et al. |
| 2010/0010311 A1* | 1/2010 | Miller et al. .................. 600/156 |
| 2010/0094081 A1* | 4/2010 | Rothe et al. .................. 600/104 |
| 2010/0130836 A1* | 5/2010 | Malchano et al. .................. 600/301 |
| 2011/0060227 A1 | 3/2011 | Saadat |
| 2011/0060298 A1 | 3/2011 | Saadat |
| 2011/0144576 A1 | 6/2011 | Rothe et al. |
| 2013/0131448 A1 | 5/2013 | Saadat et al. |
| 2013/0172726 A9 | 7/2013 | Saadat et al. |

FOREIGN PATENT DOCUMENTS

| | | |
|---|---|---|
| EP | 0842673 | 5/1998 |
| EP | 0301288 A1 | 2/1999 |
| JP | 59093413 A | 5/1984 |
| JP | 59-181315 | 10/1984 |
| JP | 01-221133 | 9/1989 |
| JP | 03-284265 | 12/1991 |
| JP | 05-103746 | 4/1993 |
| JP | 09-051897 | 2/1997 |
| JP | 11-299725 | 11/1999 |
| JP | 2001-258822 | 9/2001 |
| WO | WO 92/21292 | 12/1992 |
| WO | WO 94/07413 | 4/1994 |
| WO | WO 95/03843 | 2/1995 |
| WO | WO 97/40880 | 11/1997 |
| WO | WO 98/18388 | 5/1998 |
| WO | WO 00/24310 | 5/2000 |
| WO | WO 01/49356 | 7/2001 |
| WO | WO 01/72368 | 10/2001 |
| WO | WO 02/30310 | 4/2002 |
| WO | WO 03/037416 | 5/2003 |
| WO | WO 03/039350 | 5/2003 |

(56) References Cited

FOREIGN PATENT DOCUMENTS

| WO | WO 03/053491 | 7/2003 |
|----|---|---|
| WO | WO 03/073942 | 9/2003 |
| WO | WO 03/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

U.S. Appl. No. 11/775,771, filed Jul. 10, 2007 in the name of Saadat et al., Non-final Office Action mailed Aug. 27, 2010.
U.S. Appl. No. 11/828,267, filed Jul. 25, 2007 in the name of Saadat et al., final Office Action mailed Sep. 16, 2010.
Avitall, A Catheter System to Ablate Atrial Fibrillation in a Sterile Pericarditis Dog Model, PACE, vol. 17, p. 774, 1994.
Avitall, Right-Sided Driven Atrial Fibrillation in a Sterile Pericarditis Dog Model, PACE, vol. 17, p. 774, 1994.
Avitall, Vagally Mediated Atrial Fibrillation in a Dog Model can be Ablated by Placing Linear Radiofrequency Lesions at the Junction of the Right Atrial Appendage and the Superior Vena Cava, PACE, vol. 18, p. 857, 1995.
Baker, Nonpharmacologic Approaches to the Treatment of Atrial Fibrillation and Atrial Flutter, J. Cardiovasc. Electrophysiol., vol. 6, pp. 972-978, 1995.
Bhakta, Principles of Electroanatomic Mapping, Indian Pacing & Electrophysiol J., vol. 8, No. 1, pp. 32-50, 2008.
Bidoggia, Transseptal Left Heart Catheterization: Usefulness of the Intracavitary Electrocardiogram in the Localization of the Fossa Ovalis, Cathet Cardiovasc Diagn., vol. 24, No. 3, pp. 221-225, 1991.
Bredikis, Surgery of Tachyarrhythmia: Intracardiac Closed Heart Cryoablation, PACE, vol. 13, pp. 1980-1984, 1990.
Cox, Cardiac Surgery for Arrhythmias, J. Cardiovasc. Electrophysiol., vol. 15, pp. 250-262, 2004.
Cox, Five-Year Experience With the Maze Procedure for Atrial Fibrillation, Ann. Thorac. Surg., vol. 56, pp. 814-824, 1993.
Cox, Modification of the Maze Procedure for Atrial Flutter and Atrial Fibrillation, J. Thorac. Cardiovasc. Surg., vol. 110, pp. 473-484, 1995.
Cox, The Status of Surgery for Cardiac Arrhythmias, Circulation, vol. 71, pp. 413-417, 1985.
Cox, The Surgical Treatment of Atrial Fibrillation, J. Thorac Cardiovasc. Surg., vol. 101, pp. 584-592, 1991.
Elvan, Replication of the "Maze" Procedure by Radiofrequency Catheter Ablation Reduces the Ability to Induce Atrial Fibrillation, PACE, vol. 17, p. 774, 1994.
Elvan, Radiofrequency Catheter Ablation (RFCA) of the Atria Effectively Abolishes Pacing Induced Chronic Atrial Fibrillation, PACE, vol. 18, p. 856, 1995.
Elvan, Radiofrequency Catheter Ablation of the Atria Reduces Inducibility and Duration of Atrial Fibrillation in Dogs, Circulation, vol. 91, pp. 2235-2244, 1995.

European Patent Application No. 06734083.6 filed Jan. 30, 2006 in the name of Saadat et al., extended European Search Report mailed Jul. 1, 2009.
European Patent Application No. 06734083.6 filed Jan. 30, 2006 in the name of Saadat et al., office action mailed Oct. 23, 2009.
Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.
Hoey, Intramural Ablation Using Radiofrequency Energy Via Screw-Tip Catheter and Saline Electrode, PACE, vol. 18, p. 487, 1995.
Huang, Increase in the Lesion Size and Decrease in the Impedance Rise with a Saline Infusion Electrode Catheter for Radiofrequency, Circulation, vol. 80, No. 4, pp. II-324, 1989.
Moser, Angioscopic Visualization of Pulmonary Emboli, CHEST, vol. 77, No. 2, pp. 198-201, 1980.
Nakamura, Percutaneous Intracardiac Surgery With Cardioscopic Guidance, SPIE, vol. 1652, pp. 214-216, 1992.
Pappone, Circumferential Radiofrequency Ablation of Pulmonary Vein Ostia, Circulation, vol. 102, pp. 2619-2628, 2000.
Sethi, Transseptal Catheterization for the Electrophysiologist: Modification with a "View", J. Interv. Card. Electrophysiol., vol. 5, pp. 97-99, 2001, Kluwer Academic Publishers, Netherlands.
Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.
U.S. Appl. No. 11/828,267, filed Jul. 25, 2007 in the name of Saadat et al., Non-final Office Action mailed Jan. 14, 2010.
U.S. Appl. No. 12/117,655, filed May 8, 2008 in the name of Saadat et al., Non-final Office Action mailed Jun. 8, 2009.
Willkampf, Radiofrequency Ablation with a Cooled Porous Electrode Catheter, JACC, vol. 11, No. 2, p. 17A, 1988.
European Patent Application No. 06734083.6 filed Jan. 30, 2006 in the name of Voyage Medical, Inc., Office Action mailed Nov. 12, 2010.
U.S. Appl. No. 12/947,198, filed Nov. 16, 2010 in the name of Saadat, non-final Office Action mailed Feb. 18, 2011.
U.S. Appl. No. 12/947,246, filed Nov. 16, 2006 in the name of Saadat, non-final Office Action mailed Feb. 18, 2011.
U.S. Appl. No. 11/687,597, filed Mar. 16, 2007 in the name of Saadat, Notice of Allowance mailed Feb. 24, 2011.
U.S. Appl. No. 11/560,732, filed Mar. 16, 2007 in the name of Saadat, Notice of Allowance mailed Feb. 24, 2011.
U.S. Appl. No. 11/848,207, filed Aug. 30, 2007 in the name of Saadat et al., non-final Office Action mailed Feb. 25, 2011.
Japanese Patent Application No. 2007-554156 filed Jan. 30, 2006 in the name of Voyage Medical, Inc., Office Action mailed Feb. 15, 2011.
European Patent Application No. 07758716.0 filed Mar. 16, 2007 in the name of Voyage Medical, Inc., Supplemental European Search Report mailed Feb. 28, 2011.
U.S. Appl. No. 11/848,202, filed Aug. 30, 2007 in the name of Saadat et al., non-final Office Action mailed Mar. 11, 2011.
U.S. Appl. No. 11/763,399, filed Jun. 14, 2007 in the name of Saadat et al., non-final Office Action mailed Apr. 11, 2011.
U.S. Appl. No. 12/499,011, filed Jul. 7, 2009 in the name of Rothe et al., non-final Office Action mailed Apr. 12, 2011.
U.S. Appl. No. 12/367,019, filed Feb. 6, 2009 in the name of Miller et al., non-final Office Action mailed Apr. 22, 2011.
U.S. Appl. No. 11/959,158, filed Dec. 18, 2007 in the name of Saadat et al., non-final Office Action mailed Apr. 25, 2011.
U.S. Appl. No. 11/848,532, filed Aug. 31, 2007 in the name of Saadat et al., non-final Office Action mailed Apr. 26, 2011.
U.S. Appl. No. 11/828,281, filed Jul. 25, 2007 in the name of Peh et al., non-final Office Action mailed Apr. 27, 2011.
U.S. Appl. No. 11/961,950, filed Dec. 20, 2007 in the name of Saadat et al., non-final Office Action mailed May 9, 2011.
U.S. Appl. No. 11/961,995, filed Dec. 20, 2007 in the name of Saadat et al., non-final Office Action mailed May 9, 2011.
U.S. Appl. No. 11/962,029, filed Dec. 20, 2007 in the name of Saadat et al., non-final Office Action mailed May 9, 2011.
U.S. Appl. No. 11/828,267, filed Jul. 25, 2007 in the name of Saadat et al., non-final Office Action mailed May 11, 2011.

(56) References Cited

OTHER PUBLICATIONS

Japanese Patent Application No. 2009-500630 filed Mar. 16, 2007 in the name of Voyage Medical, Inc., Office Action mailed Apr. 27, 2011.
U.S. Appl. No. 11/775,771, filed Jul. 10, 2007 in the name of Saadat et al., final Office Action mailed May 12, 2011.
U.S. Appl. No. 11/877,386, filed Oct. 23, 2007 in the name of Saadat et al., non-final Office Action mailed May 20, 2011.
U.S. Appl. No. 11/775,819, filed Jul. 10, 2007 in the name of Saadat et al., non-final Office Action mailed May 20, 2011.
U.S. Appl. No. 11/775,837, filed Jul. 10, 2007 in the name of Saadat et al., non-final Office Action mailed May 23, 2011.
U.S. Appl. No. 12/117,655, filed May 8, 2008 in the name of Peh et al., final Office Action mailed Jun. 2, 2011.
U.S. Appl. No. 12/323,281, filed Nov. 25, 2008 in the name of Saadat et al., non-final Office Action mailed Jun. 7, 2011.
Japanese Patent Application No. 2007-554156 filed Jan. 30, 2006 in the name of Voyage Medical, Inc., Notice of Allowance mailed Jun. 13, 2011.
U.S. Appl. No. 11/259,498, filed Oct. 25, 2005 in the name of Saadat, Notice of Allowance mailed Nov. 15, 2010.
U.S. Appl. No. 11/560,742, filed Nov. 16, 2006 in the name of Saadat, Notice of Allowance mailed Nov. 15, 2010.
U.S. Appl. No. 12/464,800, filed May 12, 2009 in the name of Peh et al., non-final Office Action mailed Nov. 24, 2010.
U.S. Appl. No. 11/848,429, filed Aug. 31, 2007 in the name of Peh et al., non-final Office Action mailed Nov. 24, 2010.
European Patent Application No. 07812146.4 filed Jun. 14, 2007 in the name of Voyage Medical, Inc., European Search Report mailed Nov. 18, 2010.
European Patent Application No. 07799466.3 filed Jul. 10, 2007 in the name of Voyage Medical, Inc., European Search Report mailed Nov. 18, 2010.
U.S. Appl. No. 11/560,732, filed Nov. 16, 2006 in the name of Saadat, Notice of Allowance mailed Feb. 3, 2011.
U.S. Appl. No. 12/117,655, filed May 8, 2008 in the name of Peh et al., non-final Office Action mailed Dec. 16, 2010.
U.S. Appl. No. 12/026,455, filed Feb. 5, 2008 in the name of Saadat et al., non-final Office Action mailed Dec. 27, 2010.
European Patent Application No. 06734083.6 filed Jan. 30, 2006 in the name of Saadat et al., Examination Communication mailed May 18, 2010.
European Patent Application No. 07841754.0 filed Aug. 31, 2007 in the name of Saadat et al., Supplemental European Search Report mailed Jun. 30, 2010.
European Patent Application No. 08746822.9 filed Apr. 24, 2008 in the name of Rothe et al., European Search Report mailed Mar. 29, 2010.
European Patent Application No. 08746822.9 filed Apr. 24, 2008 in the name of Rothe et al.. Office Action mailed Jul. 13, 2010.
U.S. Appl. No. 11/259,498, filed Oct. 25, 2005 in the name of Saadat et al., Non-final Office Action mailed Feb. 25, 2010.
U.S. Appl. No. 11/560,742, filed Nov. 16, 2006 in the name of Saadat, Non-final Office Action mailed Jun. 10, 2010.
U.S. Appl. No. 11/687,597, filed Mar. 16, 2007 in the name of Saadat et al., Non-final Office Action mailed Jul. 21, 2010.
U.S. Appl. No. 12/117,655, filed May 8, 2008 in the name of Peh et al., Final Office Action mailed Mar. 1, 2010.
U.S. Appl. No. 61/286,283, filed Dec. 14, 2009 in the name of Rothe et al.
U.S. Appl. No. 61/297,462, filed Jan. 22, 2010 in the name of Rothe et al.
Uchida, Developmental History of Cardioscopes, Coronary Angioscopy, pp. 187-197, 2001, Future Publishing Co., Armonk, NY.

\* cited by examiner

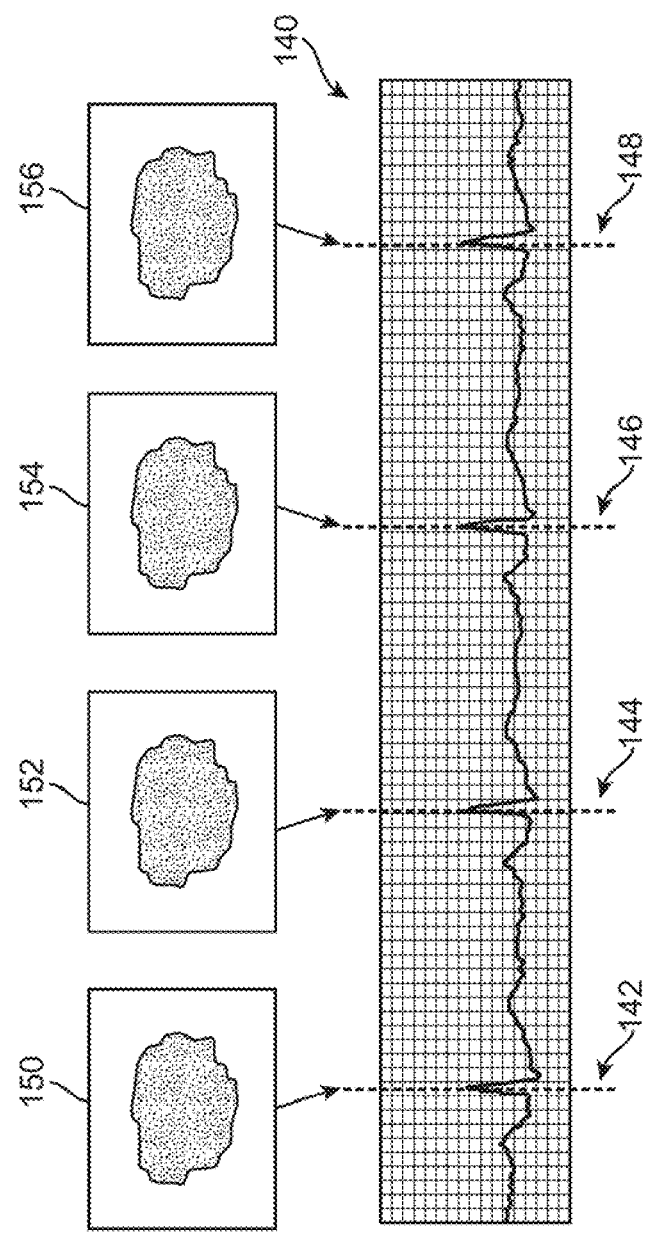

| Leison ID | Shape | RF power used for ablation | Length of time of ablation |
|---|---|---|---|
| 1 |  | 20W | 60s |
| 2 |  | 20W | 60s |
| 3 |  | 25W | 60s |
| 4 |  | 20W | 50s |
| 5 |  | 30W | 40s |

INTRAVASCULAR CATHETER WITH HOOD AND IMAGE PROCESSING SYSTEMS

CROSS-REFERENCE TO RELATED APPLICATIONS

This application claims the benefit of priority to U.S. Prov. Pat. App. 61/114,834 filed Nov. 14, 2008, which is incorporated herein by reference in its entirety.

FIELD OF THE INVENTION

The present invention relates generally to medical devices used for visualizing and/or assessing regions of tissue within a body. More particularly, the present invention relates to methods and apparatus for visualizing and/or assessing regions of tissue within a body, such as the chambers of a heart, to facilitate diagnoses and/or treatments for the tissue.

BACKGROUND OF THE INVENTION

Conventional devices for visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging. Additionally, imaging balloons are subject to producing poor or blurred tissue images if the balloon is not firmly pressed against the tissue surface because of intervening blood between the balloon and tissue.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult. Moreover, once a visual image of a tissue region is acquired in vivo, there may be additional difficulties in assessing the condition of the underlying tissue for appropriate treatments or treatment parameters.

Thus, a tissue imaging system which is able to provide real-time in vivo images and assessments of tissue regions within body lumens such as the heart through opaque media such as blood and which also provide instruments for therapeutic procedures upon the visualized tissue are desirable.

SUMMARY OF THE INVENTION

In describing the tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and an instrument translatable through the displaced blood for performing any number of treatments upon the tissue surface within the field of view. The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

In utilizing the devices and systems to access and image tissue, particular tissue regions within the body to be visualized and/or treated may undergo occasional or constant movement in vivo. For instance, organs such as the lungs constantly expand and contract while the patient undergoes respiration and other organs such as the heart constantly contract to pump blood through the body. Because of this tissue movement, acquiring a tissue image and/or other physiologic data taken at a first instance may present a condition which is inconsistent with the tissue image and/or physiologic data taken at a second instance. Accordingly, being able to acquire images and/or physiologic data of a particular tissue region at a first point during tissue movement and at additional points during subsequent tissue movements taken consistently when the tissue is similarly situated may present a more accurate representation of the condition for evaluation of the tissue region being examined and/or treated. To accurately assess and/or treat a particular tissue region despite this movement of tissue, e.g., a tissue region located within an atrial chamber within the beating heart, methods may be utilized to minimize the effect of this movement on obtained data.

One method may involve gating the acquisition of the tissue images and/or corresponding data by utilizing a reference signal produced by the body for coordinating the corresponding acquisition of information. For gated acquisition of information, such as the captured visual images of the tissue and/or corresponding physiologic parameters, the acquisition of the information may be triggered by a sensed event, e.g., the QRS complex recorded from a single heartbeat of the electrocardiogram (ECG) which corresponds to a depolarization of the right and left ventricles. Once a triggering event is identified, the system may acquire information at a specific interval and/or for a specific duration based upon that predetermined triggering event.

Although this and other examples describe the gated acquisition of information based upon the patient's ECG measurements, other gated acquisition events may also be utilized herein. For example, gated acquisition may also be utilized for obtaining images and/or other data based on chest-wall motion for respiratory-gated acquisition of data.

Another method for may involve retrospective gating of the data where information, such as visual images and/or other physiologic data, may be acquired continuously from the tissue region. This allows for the capturing of information over several cycles of the organ or tissue region of interest. By calculating or determining a timing delay within the captured data, the information can be reconstructed at one or more specified points over many heart beats relative to a predetermined reference or triggering signal. This may allow for a "snapshot" of the heart to be reconstructed at a specific phase within the cardiac cycle with the information for this "snapshot" acquired over several beating cycles which may or may not have occurred at regular intervals.

Ablation treatment of various tissue regions may also be optimized by determining the thickness of the tissue region to be treated and adjusting the ablation parameters accordingly based upon this thickness. Aside from tissue thickness and ablation parameters, it may be also useful to monitor the temperature and/or electrical potential of the tissue surface during the ablative process.

Aside from or in addition to the different modalities for monitoring tissue parameters, visually assessing the tissue region undergoing ablation may present difficulties in distinguishing between different regions of the tissue due to limitations in the imaging sensors or equipment. One method for improving the visual images of the imaged tissue for assessment by the user may include adjusting the contrast of the captured images. Contrast allows for different tissue regions to be distinguished visually from one another within an image or video. Digital imaging systems such as CMOS image sensors or CCD camera systems have light sensitivities which vary with the wavelength of light. Thus, altering the chromaticity or color of illumination used during imaging could emphasize or de-emphasize certain colors within the imaged field or the change in illumination color composition could target the sensitivity of the image sensor.

With the detection of multiple lesions along a tissue region, the unique shape of each lesion may be used to determine the "address" of that particular lesion. An edge finding, texture classification, or morphology algorithm may be used to determine the outline, surface pattern, or shape of the lesion from the visual information provided by the visualization device. This information and/or an image depicting the ablation lesion is then constructed into an array and tagged with the appropriate data such as the RF power and the length of time ablation took place to create the particular lesion. Alternatively, lesion identification may be accomplished via the usage of color comparison algorithms and/or biological markers on the lesions among other identifiers. This information may be particularly useful for re-identification, comparison and mapping of all lesions on the tissue surface.

When providing real-time visual images for the purposes of tissue diagnosis or treatment, it may be useful to overlay relevant information to aid the physician during diagnosis and/or treatment. Any number of physiologic or treatment parameters may be overlaid directly upon the monitor for display to the user to facilitate assessment or treatment, e.g., for estimating the depth of the lesion formed. In various examples, treatment information (e.g., positional information, applied power levels, time of ablation treatment, etc.) may be superimposed on the image of lesion or any other additional information (e.g., applied voltage, tissue thickness, etc.) may also be displayed upon the monitor for display to the user.

Yet another example of an informational overlay which may facilitate tissue treatment assessment may incorporate the distance of a tissue region to be treated (or undergoing treatment) to a predetermined anatomical object or location. It is also possible to overlay information relating to particular metrics on the monitor during visualization or ablation. Such overlays may be utilized to determine, e.g., the surface size of the lesion precisely to facilitate physician assessment of lesion size. It may also be used to accurately measure anatomical features in the body.

Aside from measuring anatomical features, another feature which physicians may utilize with the captured visual images of tissue may also include the monitoring of changes in color of a lesion formed over time. Tissue color may be used as a good indicator of the stage of completion of the lesion forming process as normal, unablated myocardial tissue is characteristically pink or red in color. Having these images simultaneously displayed may provide contextual information to the user in determining whether sufficient ablation had occurred in the tissue being treated.

Additionally and/or alternatively, a processor may control the flow of the purging fluid which may also be used to conduct a current to the tissue to be treated. It is generally desirable to deliver the lowest amount of saline to the patient through the hood as an excessive flow of saline may cause the balance of electrolytes in the body to fluctuate potentially resulting in hyponatremia. Yet another parameter utilizing the captured visual images during tissue ablation may include the detection of bubbles during ablation. The formation of bubbles may be visible on the monitor near or at the edges of the visual field and these bubbles may be generally indicative of high rates of heating, over-blanching of tissue, or a potential steam popping. The visual image may be processed by a processor to find locations of any "hotspots", i.e., areas of high reflection, which may be indicative of the presence of bubbles.

In yet another example for processing captured visual images of tissue regions, the region being visualized may move continually making it difficult to observe the tissue or to perform any procedures upon the tissue. Such movement can be monitored visually by several methods such that the user is able to determine an appropriate time to begin a procedure. With the distance of hood movement known, a procedure may be initiated and/or stopped appropriate each time the hood is expected to move such that treatment may be synchronized according to hood and tissue movement.

In yet another example of utilizing the captured images, bubbles may be visible in the field of view and thus alert the user that the hood positioning along the tissue may require readjustment.

BRIEF DESCRIPTION OF THE DRAWINGS

FIG. 8B shows an example of how visual images of tissue may be captured at coordinated intervals.

DETAILED DESCRIPTION OF THE INVENTION

Reconfiguring a tissue visualization and treatment device from a low profile delivery configuration for intravascular delivery through the vessels of a patient to a deployed and expanded configuration may subject the distal end effector used for visualization and/or treatment, such as energy delivery, to potentially severe mechanical stresses (e.g., torsion, compression, tension, shearing, etc.). For example, a reconfigurable hood which undergoes a shape change from its collapsed configuration to an expanded conical shape may utilize a distensible, collapsible, and/or reconfigurable substrate which may utilize electrode placement and electrical connection assemblies which are robust and able to withstand such stresses. Such electrical connection assemblies may be shielded or insulated from contacting other structures so as to present a smooth or unobstructive profile for reconfiguring with the hood.

Turning now to the tissue-imaging and manipulation apparatus upon which one or more electrodes may be positioned and which is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
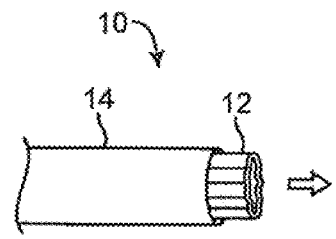
FIG. 1A shows a side view of one variation of a tissue imaging apparatus during deployment from a sheath or delivery catheter.
Figure 1B:
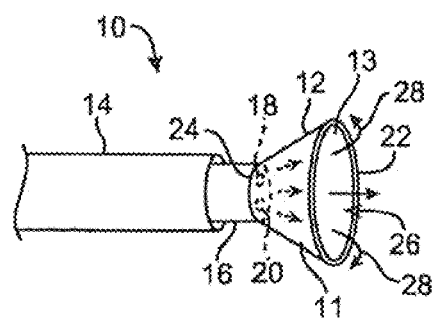
FIG. 1B shows the deployed tissue imaging apparatus of FIG. 1A having an optionally expandable hood or sheath attached to an imaging and/or diagnostic catheter.
Figure 1C:
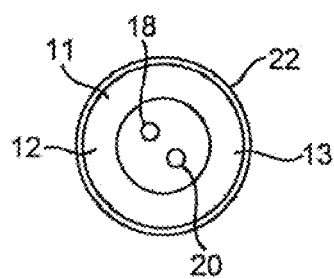
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
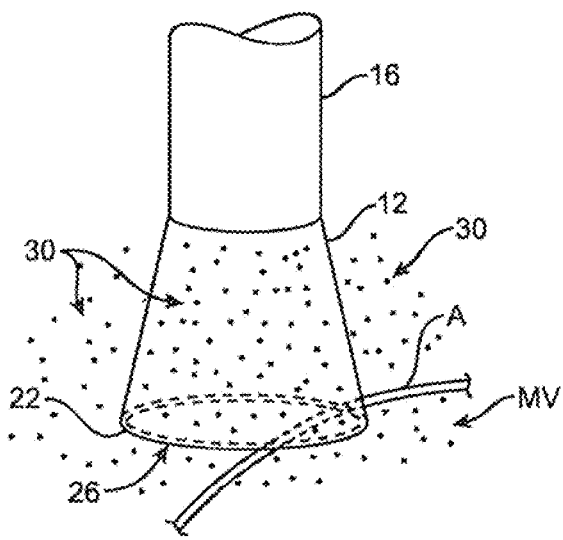
FIGS. 2A and 2B show one example of a deployed tissue imager positioned against or adjacent to the tissue to be imaged and a flow of fluid, such as saline, displacing blood from within the expandable hood.
Figure 2B:
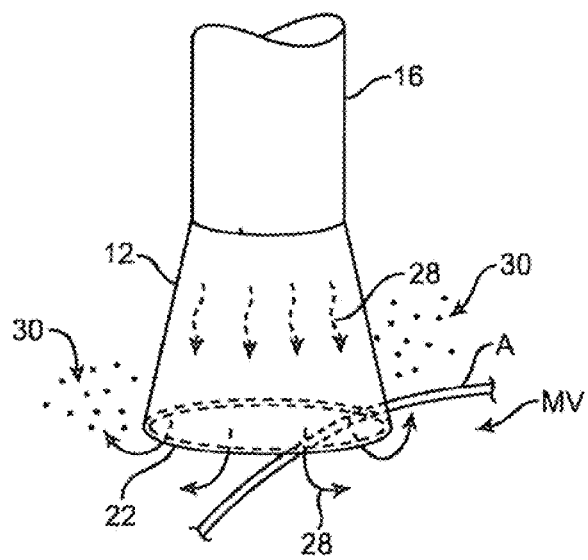

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
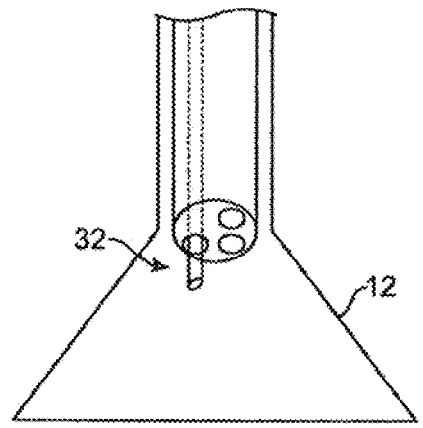
FIGS. 3A and 3B show examples of various visualization imagers which may be utilized within or along the imaging hood.
Figure 3B:
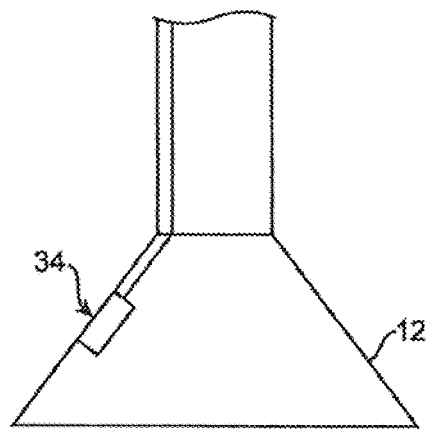

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
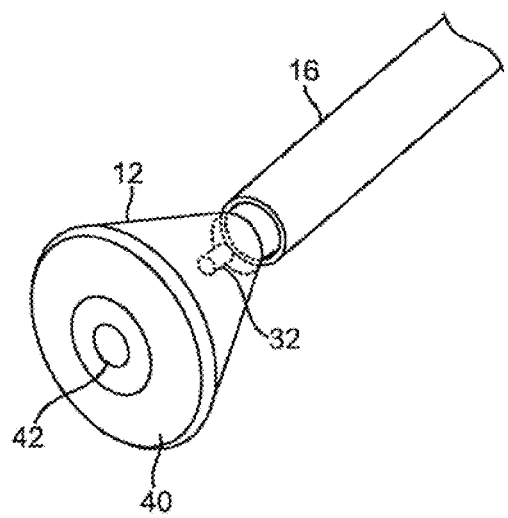
FIGS. 4A and 4B show perspective and end views, respectively, of an imaging hood having at least one layer of a transparent elastomeric membrane over the distal opening of the hood.
Figure 4B:
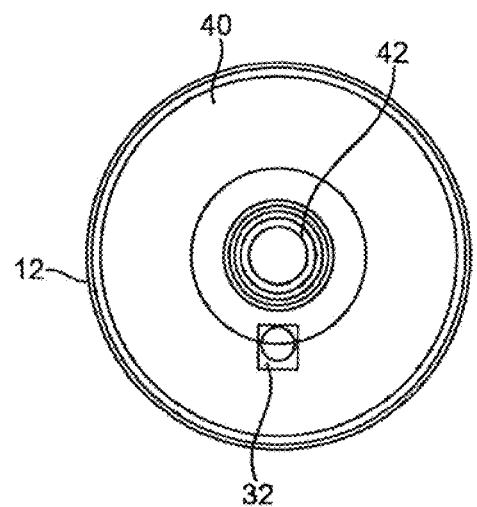

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
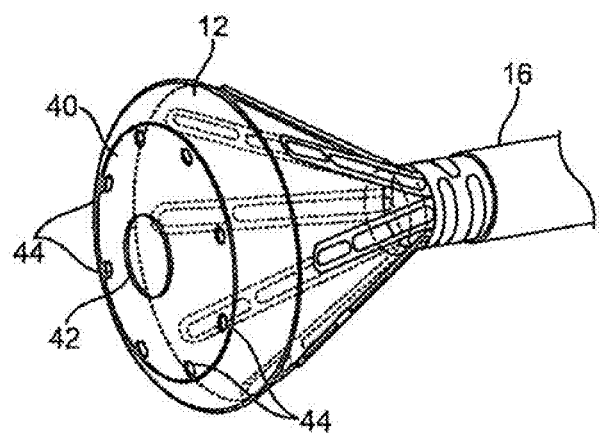
FIGS. 5A and 5B show perspective and end views, respectively, of an imaging hood which includes a membrane with an aperture defined therethrough and a plurality of additional openings defined over the membrane surrounding the aperture.
Figure 5B:
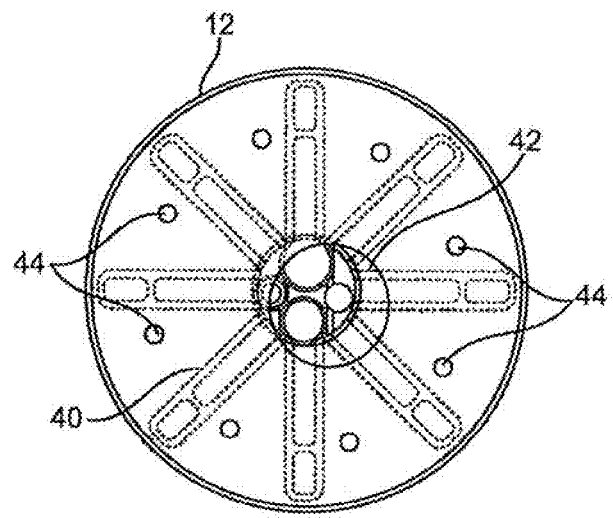

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. 2006/0184048 A1), which is incorporated herein by reference in its entirety.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A1), which is incorporated herein by reference in its entirety. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), which is incorporated herein by reference in its entirety.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

Turning now to the electrode assemblies and connection systems utilized with the collapsible hood, various examples are described herein which illustrate variations for electrode positioning along the hood which may minimize or reduce the degree of stress imparted to the electrode assemblies. These electrodes (e.g., electrode pairs) may be used to deliver electrical energy such as radio-frequency energy to tissue in direct contact with or in proximity to the electrodes to form lesions upon the tissue surface as well as underlying tissue regions. Additionally, the electrodes or electrode pairs may be positioned about the hood in a uniform or non-uniform manner depending upon the desired configuration. Moreover, these electrodes may also be used to deliver energy into and/or through the purging fluid which may contact the electrodes for conducting the energy through the fluid and into the underlying tissue region being treated. Alternatively, one or more of these electrodes may also be used to detect and/or measure any electrophysiological activity of the contacted tissue prior to, during, or after tissue treatment.

While specific examples of the visualization and treatment hood are shown herein, other variations and examples of hoods and tissue treatment systems may be utilized with the devices and methods described herein. For example, the hoods, systems, and other features as described in Ser. No. 11/259,498 filed Oct. 25, 2005 (U.S. Pat. Pub. 2006/0184048 A1); Ser. No. 11/775,837 filed Jul. 10, 2007 (U.S. Pat. Pub. 2008/0009747 A1); Ser. No. 11/828,267 filed Jul. 25, 2007 (U.S. Pat. Pub. No. 2008/0033290 A1); Ser. No. 12/118,439 filed May 9, 2008 (U.S. Pat. Pub. 2009/0030412 A1); Ser. No. 12/201,811 filed Aug. 29, 2008 (U.S. Pat. Pub. 2009/0062790 A1); and Ser. No. 12/209,057 filed Sep. 11, 2008 (U.S. Pat. Pub. 20090076498 A1), may be utilized herewith. Each of these applications is incorporated herein by reference in its entirety.

In particular, such assemblies, apparatus, and methods may be utilized for treatment of various conditions, e.g., arrhythmias, through ablation under direct visualization. Details of examples for the treatment of arrhythmias under direct visualization which may be utilized with apparatus and methods described herein are described, for example, in U.S. patent application Ser. No. 11/775,819 filed Jul. 10, 2007 (U.S. Pat. Pub. No. 2008/0015569 A1), which is incorporated herein by reference in its entirety. Variations of the tissue imaging and manipulation apparatus may be configured to facilitate the application of bipolar energy delivery, such as radio-frequency (RF) ablation, to an underlying target tissue for treatment in a controlled manner while directly visualizing the tissue during the bipolar ablation process as well as confirming (visually and otherwise) appropriate treatment thereafter.

Figure 6:
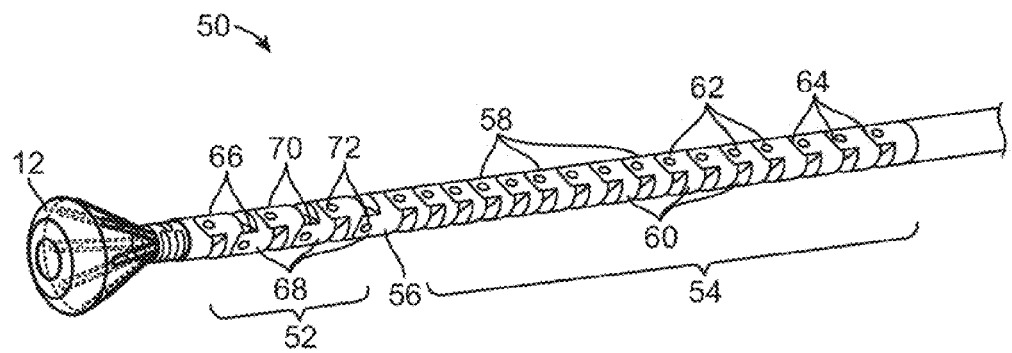
FIG. 6 shows a perspective assembly view of the steerable section of a catheter having a distal section with connected links configured to allow for multi-directional articulation, e.g., four-way articulation, and a proximal section with connected links configured to allow for articulation within a single plane, e.g., one-way articulation.

Turning now to the perspective assembly view of FIG. 6, one variation of an articulatable deployment catheter 50 is shown which comprises a distal steerable section 52 and a proximal steerable section 54 located proximally of the distal steerable section 52. Further details of the deployment catheter 50 which may be used herein may be seen in further detail in U.S. patent application Ser. No. 12/108,812 filed Apr. 24, 2008 (U.S. Pat. Pub. No. 2008/0275300 A1), which is incorporated herein by reference in its entirety. An intervening link 56 may couple the sections 52, 54 to one another and provide a terminal link to which one or more pull wires may be attached in controlling one or both sections. The distal steerable section 52 may utilize individual links 66 which allow for the section 52 to be articulated in a variety of different directions and angles, e.g., four-way steering, to enable omni-direction articulation. The individual links 66 may accordingly utilize a body member 68 having a pair of yoke members 70 positioned opposite to one another and extending distally from the body member 68 and each defining an opening. A pair of pins 72 may each extend radially in opposing directions from body member 68 and in a perpendicular plane relative to a plane defined by the yoke members 70. The pins 72 of each link 66 may be pivotably received by the yoke members 70 of an adjacent link 66 such that the pins 72 and yoke members 70 are joined in an alternating manner. This alternating connection allows for the serially aligned links 66 to be articulated omni-directionally.

The links 58 of the proximal steering section 54 may also comprise a pair of yoke members 62 positioned opposite to one another and extending distally from body member 60. However, the pins 64 may extend radially in opposing directions while remaining in the same plane as that defined by yoke members 62. When joined together in series, each pin 64 of each link 58 may be pivotably received by the yoke members 62 of an adjacent link 58. Yet when joined, the composite proximal steering section 54 may be constrained to bend planarly within a single plane relative to the rest of the deployment catheter.

The combined distal steerable section 52 and a proximal steerable section 54 results in a proximal steering section which can be articulated in a single plane to retroflex the entire distal assembly and a distal steering section which can then be articulated any number of directions, e.g., four-way steering, to access anatomical structures within the heart or any other lumen. The assembly may thus be used, e.g., to create circumferential lesions around the ostia of the pulmonary veins in the left atrium while the underlying tissue remains under direct visualization through the hood.

Figure 7:
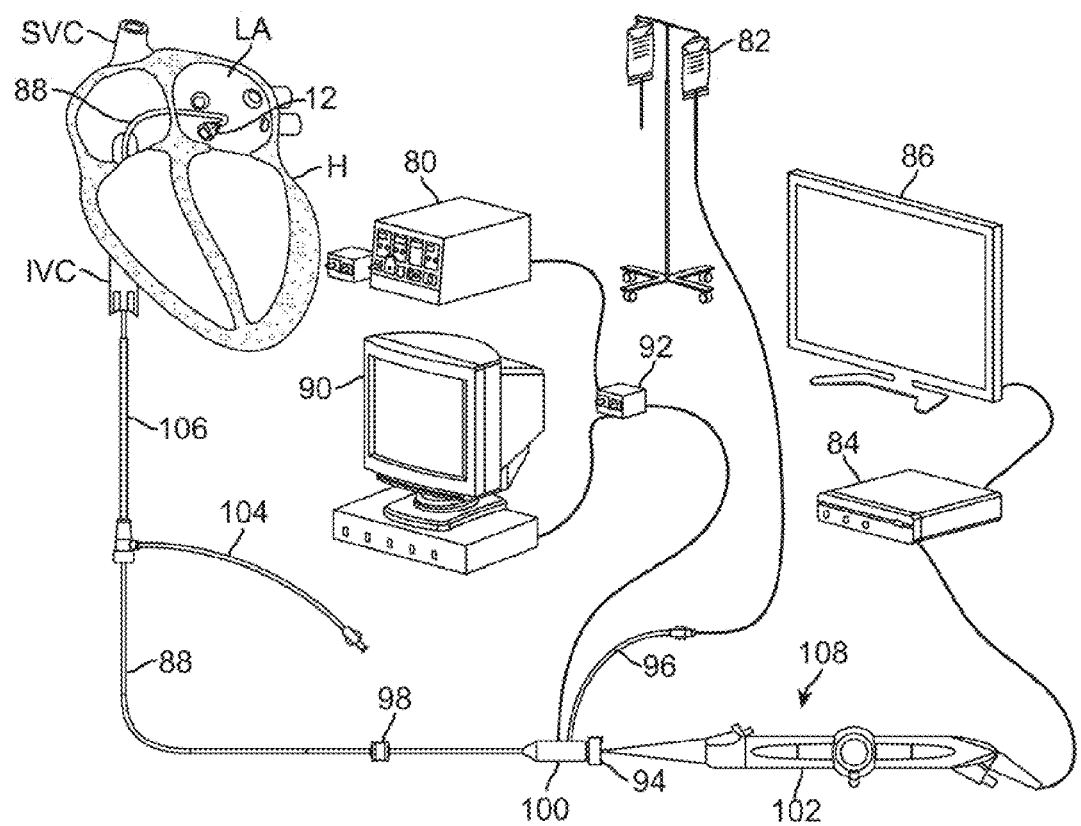
FIG. 7 illustrates an assembly view of a visualization and treatment system advanced intravascularly into a patient's heart for diagnosis and/or treatment.

In utilizing the catheter 50 or other suitable catheter system, FIG. 7 shows an illustrative assembly of how a visualization catheter system may be configured and advanced intravascularly within a patient. Further details of the system which may be used herein may be seen in further detail in U.S. patent application Ser. No. 12/323,281 filed Nov. 25, 2008 (U.S. Pat. Pub. No. 2009/0143640 A1), which is incorporated herein by reference in its entirety.

FIG. 7 illustrates a perspective assembly view of an endoscope 108 introduced within seal 94 and deployment catheter 88. Hood 12 can be first collapsed by hood retraction control 98 while saline is purged through hood 12 to ensure no bubbles are trapped inside hood 12. Catheter 88 may be advanced within introducer sheath 106 for deployment within the patient body. Additionally, introducer sheath 106 may further include a fluid irrigation port 104 extending from sheath 106 for coupling to a fluid reservoir or for providing access to other instruments into the patient body. The variation shown also illustrates an example where an additional endoscope handle interface may be attached to hub 100 for facilitating coupling and de-coupling to endoscope handle 102.

Hood 12 and deployment catheter 88 may be advanced through introducer sheath 106 into the patient's vasculature, e.g., through the inferior vena cava IVC and transseptally into the left atrium LA of the patient's heart H, where tissue regions may be treated, such as lesion creation around the ostia of the pulmonary veins for treatment of atrial fibrillation. Once hood 12 has been advanced into the left atrium LA, hood 12 may be deployed to expand for visualization and tissue treatment. Hood 12 may be purged via saline fluid from reservoir 82 introduced through port 96 while an electrode assembly along hood 12 may be utilized to detect, e.g., ECG signals 90, or to ablate tissue via generator 80. These electrical signals may be detected and/or delivered via the electrode assembly which may be electrically coupled through catheter 88 to a processor and/or video display, e.g., electrocardiogram (ECG) display, via junction 92, which may also be electrically coupled to generator 80 for providing power, e.g., RF energy, to the electrode assembly. The underlying tissue may be visualized via the endoscope imaging assembly which may in turn be coupled to video processor assembly 84 which may capture and process the detected images within hood 12 for display upon monitor 86. Alternatively, hood 12 may be purged via fluid introduced through a fluid lumen defined through the endoscope itself.

The working channel of the endoscope and/or irrigation port can also be used to introduce guidewires, needles (such as transseptal or biologics delivery needles), dilators, ablation catheters (such as RF, cryo, ultrasound, laser and microwave), temperature monitoring probes, PFO closure devices, LAA closure implants, coronary artery stents, or other implantable devices or tools for performing diagnosis and/or treatment of the imaged target tissue. These lumens can also be used for the suction and/or evacuation of blood clots and/or any tissue debris as well as for the injection of contrast media for fluoroscopic imaging.

In utilizing the devices and systems to access and image tissue, particular tissue regions within the body to be visualized and/or treated may undergo occasional or constant movement in vivo. For instance, organs such as the lungs constantly expand and contract while the patient undergoes respiration and other organs such as the heart constantly contract to pump blood through the body. Because of this tissue movement, acquiring a tissue image and/or other physiologic data taken at a first instance may present a condition which is inconsistent with the tissue image and/or physiologic data taken at a second instance. Accordingly, being able to acquire images and/or physiologic data of a particular tissue region at a first point during tissue movement and at additional points during subsequent tissue movements taken consistently when the tissue is similarly situated may present a more accurate representation of the condition for evaluation of the tissue region being examined and/or treated. To accurately assess and/or treat a particular tissue region despite this movement of tissue, e.g., a tissue region located within an atrial chamber within the beating heart, methods may be utilized to minimize the effect of this movement on obtained data.

One method may involve gating the acquisition of the tissue images and/or corresponding data by utilizing a reference signal produced by the body for coordinating the corresponding acquisition of information. For gated acquisition of information, such as the captured visual images of the tissue and/or corresponding physiologic parameters, the acquisition of the information may be triggered by a sensed event, e.g., the QRS complex recorded from a single heartbeat of the electrocardiogram (ECG) which corresponds to a depolarization of the right and left ventricles. Once a triggering event is identified, the system may acquire information at a specific interval and/or for a specific duration based upon that predetermined triggering event.

Although this and other examples describe the gated acquisition of information based upon the patient's ECG measurements, other gated acquisition events may also be utilized herein. For example, gated acquisition may also be utilized for obtaining images and/or other data based on chest-wall motion for respiratory-gated acquisition of data.

Another method for may involve retrospective gating of the data where information, such as visual images and/or other physiologic data, may be acquired continuously from the tissue region. This allows for the capturing of information over several cycles of the organ or tissue region of interest. By calculating or determining a timing delay within the captured data, the information can be reconstructed at one or more specified points over many heart beats relative to a predetermined reference or triggering signal. This may allow for a "snapshot" of the heart to be reconstructed at a specific phase within the cardiac cycle with the information for this "snapshot" acquired over several beating cycles which may or may not have occurred at regular intervals.

Generally, when two-dimensional images of a moving organ, such as the heart, are captured the images are built up over time in synchronization with respect to the movement of the organ. For example, CT images of the heart may be captured in synchronization with a sensed ECG signal such that all the CT image slices are generated at the same point during the heart cycle. In the absence of such synchronization, the three-dimensional images may be blurred rendering them unsuitable for analysis. Additionally and/or alternatively, images of the organs may also be synchronized with the respiratory cycle, as previously mentioned.

Figure 8A:
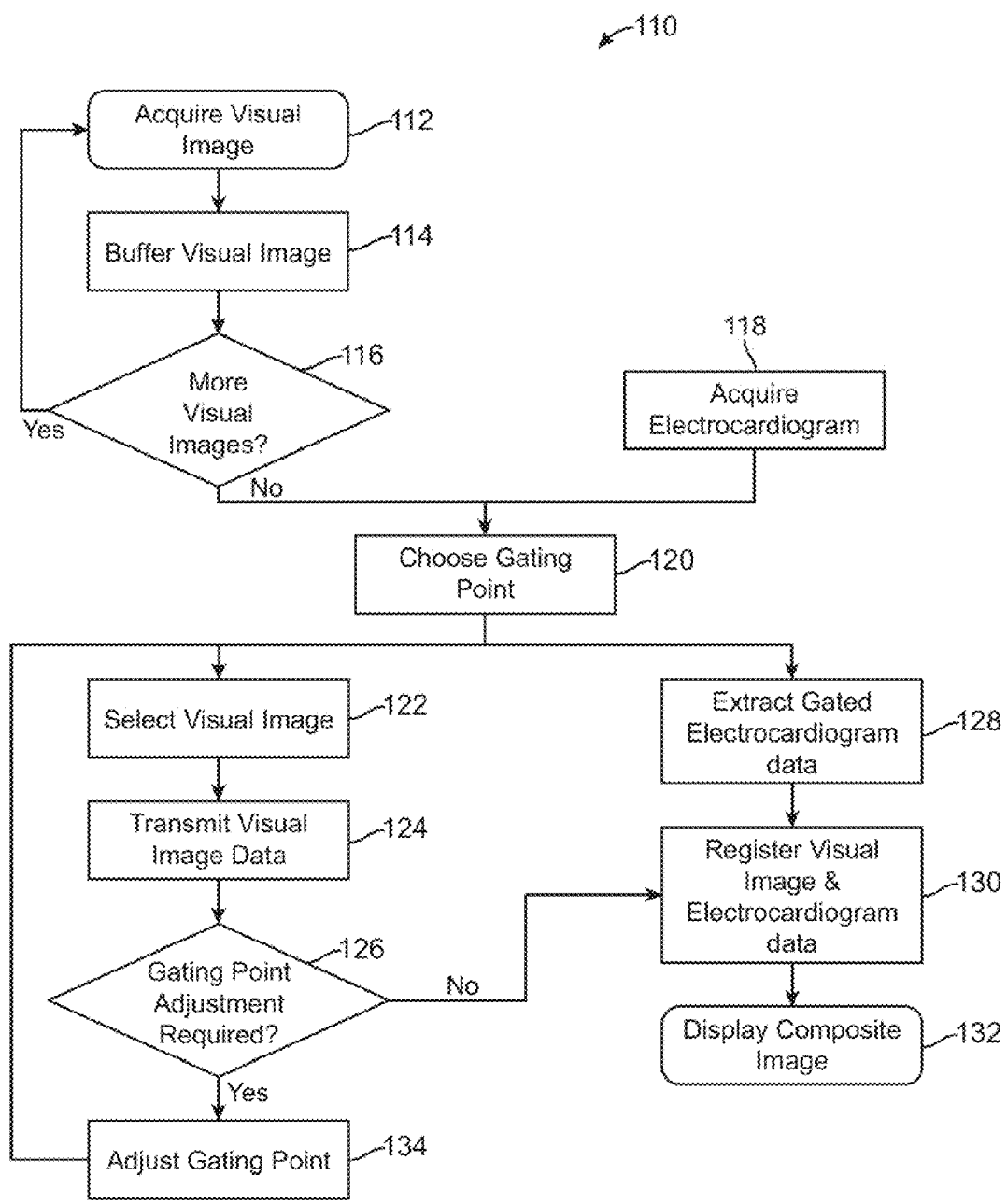
FIG. 8A shows a flowchart illustrating one example for synchronizing visual images of tissue with electrocardiogram data to capture images of consistent regions of tissue.

When anatomical features, electro-anatomical maps, or any other real-time data is to be registered against real-time visual images of the heart or any other moving organ, a determination of which cycle the image was acquired may be used to achieve proper registration between the data and the corresponding image. Generally, one or more visual images may be collected simultaneously with the sensed ECG data. An example for synchronizing data, in this case ECG data, with real-time visual images is illustrated in the flowchart 110, as shown in FIG. 8A. The hood 12 may be advanced intravascularly, e.g., into a heart chamber such as the left atrial chamber, where it may be presented against a tissue region of interest moving as the heart continues to beat. The hood 12 may be cleared, as previously described, and one or more images of the underlying tissue may be acquired 112. These one or more images may be buffered 114 and multiple images may be acquired 116 until sufficient images are captured.

While the visual images are captured, one or more sensors located along the hood 12 or separately upon the patient may be used to simultaneously detect and record ECG data 118. In the event that a sufficient number of images have been captured, a gating point may be selected 120 such as during an R wave of the QRS Complex, although any number of other physiologic triggering points may be utilized. With the gating point determined, a controller or processor may select the appropriate visual image 122 which was captured correspondingly and transmit the visual image data 124 for comparison. The controller or processor may then adjust the gating point 126, if necessary, in which case the gating point may be appropriately adjusted 134 by selecting another appropriate image. Should the gating point be adjusted to a different gating point, a new set of corresponding visual images may be displayed. Such synchronization may allow for visual analysis of the tissue that is imaged as the impact on the image quality due to the movement of the tissue may be greatly reduced (for example, due to the expansion and contraction of the heart). While the visual images are selected and transmitted, the recorded ECG data may be extracted 128 and the data may be registered with the corresponding visual image 130. The final extracted image with the corresponding ECG data may then be displayed as a composite image 132 to the user.

As illustrated in the example of FIG. 8B, a detected and recorded ECG measurement 140 of a patient is shown and displayed over several cycles of the heart beating. While the ECG measurement 140 was recorded, the visual images of the tissue region of interest were simultaneously captured as well. In utilizing the R wave of the QRS Complex, in this example, as the triggering or gating point, the visual images of the tissue region captured at those corresponding times may be extracted and registered corresponding to each gating point. The image at each gating point may then be displayed to the user as a composite image, as shown. Thus, the first gating point 142 shown on the ECG measurement 140 may have a first corresponding image 150 displayed accordingly and the second gating point 144 may have a second corresponding image 152 displayed accordingly as well. Likewise, third gating point 146 may have third corresponding image 154 displayed while fourth gating point 148 may have fourth corresponding image 156 displayed, and so on. In this manner, the visualized tissue region may be compared between captured images to provide a more accurate representation of the tissue in any particular state.

Moreover, cardiac-gating of information allows for piecewise data acquisition over multiple heart beats to create a global view of the heart at a single phase within the cardiac cycle. For example, within the left ventricle, the end-systolic phase of the cardiac cycle represents the maximum contraction of the ventricle. Therefore, the ventricular cavity defines its relative smallest volume at this phase of the cardiac cycle. Likewise, the end-diastolic phase of the cardiac cycle represents the end of the filling period of the left ventricle with blood. The ventricle is at its maximum or near-maximum volume at this phase.

Throughout each cardiac cycle, a point on the endocardial surface may be displaced in three-dimensional space between these two phases of the cardiac cycle. To create a three-dimensional map of the endocardial surface during end-diastole, individual mapping points may include the relative position (e.g., X, Y, Z coordinates) to be consistently captured at the point during the cardiac cycle relative to the reference or gating signal, such as the ECG signal. These methods could also be applied to the captured visualization information. In order to capture an image at the same point in the cardiac cycle, a global reference such as the ECG signal may be used. Based on timing data relative to a specific event such as the QRS Complex on the ECG recording, the image could be correspondingly registered by calculating the timing delays within the system for data acquisition and processing. These delays could shift the two data streams relative to one another.

In treating a tissue region, e.g., via application of energy such as RF energy to create lesions, one physiologic characteristic which is usually not readily available to physicians is the thickness of the tissue at a desired lesion location. It may be generally useful to know the thickness of the tissue in facilitating lesion formation by applying an appropriate level of energy to prevent excessive lesion formation (e.g., lesions which are larger and/or deeper than desired) in order to prevent damage to surrounding tissue or anatomy. Information on the tissue thickness may also be useful to the physician so that the optimal parameters for ablation may be determined with respect to the speed of the ablation formation to safely reduce procedural time.

Figure 9A:
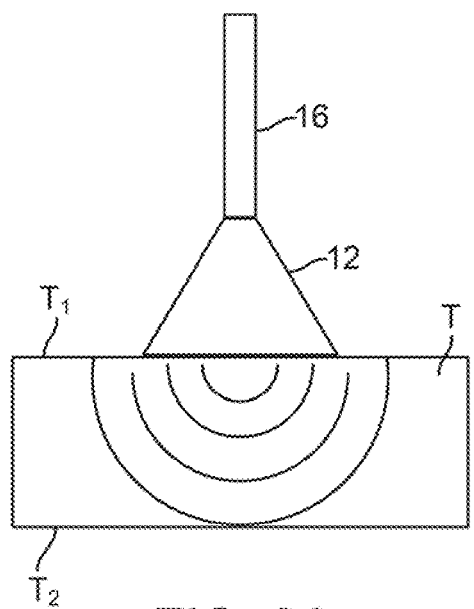
FIGS. 9A and 9B show, respectively, a schematic illustration and representative graph of a tissue region undergoing ablation and the temperature differential resulting between the tissue surface and underlying tissue region.
Figure 9B:
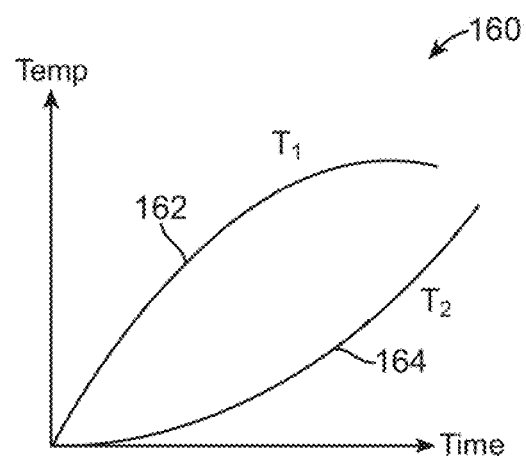

One of the difficulties in determining appropriate ablation treatment parameters through the hood 12 may be due to the temperature gradient formed through the tissue thickness during ablation treatment. For example, FIG. 9A illustrates an example of hood 12 placed against a tissue region T to be ablated. As energy is conducted through hood 12 and into the underlying tissue, a temperature differential is formed between the tissue surface $T_1$ and a region of underlying tissue $T_2$. As heat is conducted from the tissue surface $T_1$ down through the tissue region T, tissue surface $T_1$ may undergo ablation first as its temperature rises quickly during ablation treatment, as indicated by curve 162, relative to the temperature of the underlying tissue $T_2$ which rises slowly over time, as indicated by curve 164, shown in the ablation time versus temperature graph 160 of FIG. 9B.

Figure 9C:
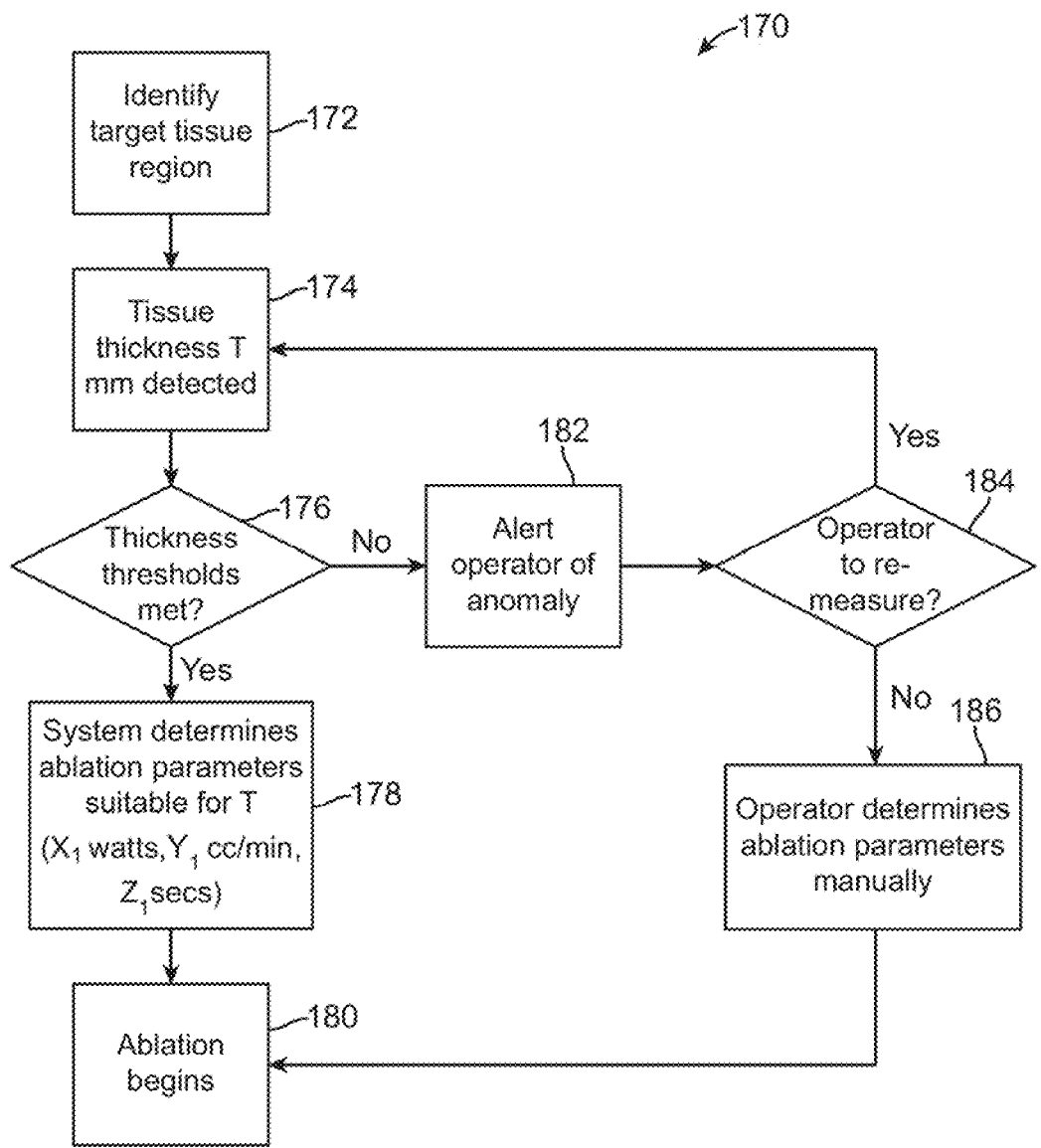
FIG. 9C shows a flowchart illustrating one example for determining suitable ablation parameters for a given thickness of tissue.

One example for determining the thickness of a tissue region to be treated and for selecting ablation parameters based on this thickness is illustrated in the flowchart 170 of FIG. 9C. With the tissue region to be treated identified visually (or through other modalities) 172, the tissue thickness may be detected 174 utilizing, e.g., hood 12 having one or more ultrasonic transducers positioned upon hood 12 or its distal membrane in contact with the underlying tissue. For example, prior to the initiation of tissue ablation, the one or more transducers may be placed against the tissue surface to be treated and ultrasonic signals may be emitted into the tissue. The emitted signals may be reflected by any underlying obstructions or tissue interfaces such that the return signals received by the transducer or receiver may be automatically processed by a processor to analyze the return signals for peaks of the ultrasonic waves received and the time intervals between them to determine a thickness of the underlying tissue. Examples of ultrasound use with hood 12 are shown and described in greater detail in U.S. patent application Ser. No. 12/118,439 filed May 9, 2008 (U.S. Pat. Pub. 2009/0030412 A1), which is incorporated herein by reference in its entirety. Alternatively, tissue thickness may also be determined by, e.g., sensor triangulation techniques, trans-esophageal echocardiography or any other methods.

A nominal tissue thickness may be programmed into a processor by the user to set a threshold tissue thickness for safely performing tissue ablation. The detected tissue thickness may then be compared against this nominal thickness threshold 176. In the event that the detected thickness exceeds this threshold tissue thickness, the controller may automatically determine the appropriate ablation parameters suitable for this detected thickness 178 such as, power levels (e.g., Watts), flow rate of the purging/conductive fluid through the hood (e.g., cc/min), ablation treatment times (e.g., sec), etc. (which may be available on a table of tissue depth versus power, flow rate, ablation duration, etc.). This determination may be performed automatically by the system or by the user and ablation may be started 180 either automatically or initiated by the user. In the event that the detected tissue thickness fails to meet the threshold tissue thickness, the system may alert the user 182 who may then re-measure the tissue thickness 184. If the re-measured tissue thickness exceeds the nominal tissue thickness, ablation may proceed, as previously described, or the operator may determine the ablation parameters manually 186 and then initiate ablation 180.

Additional examples of devices and methods which may be utilized with the systems described herein are further shown in U.S. Pat. Pub. 2007/0106146 A1, which is incorporated herein by reference in its entirety.

Aside from tissue thickness and ablation parameters, it may be also useful to monitor the temperature of the tissue surface during the ablative process. Ablation of tissue is typically performed such that it causes irreversible tissue damage to selected regions of tissue. The temperature at which irreversible tissue damage typically occurs is around 53° C. depending on the tissue thickness. Excessively high temperatures may give rise to the possibility of bubble formation on the tissue (which may pop as steam) or tissue charring. Steam pops, which may burst with an audible popping sound, may disrupt the myocardium and cause perforations on the tissue surface potentially leading to complications, such as cardiac tamponade, which may cause the heart to pump decreasing amount of blood. Charring of tissue may also allow thrombus formation which may embolize and potentially lead to stroke, ischemia, and/or myocardial infarction among other things.

Figure 10:
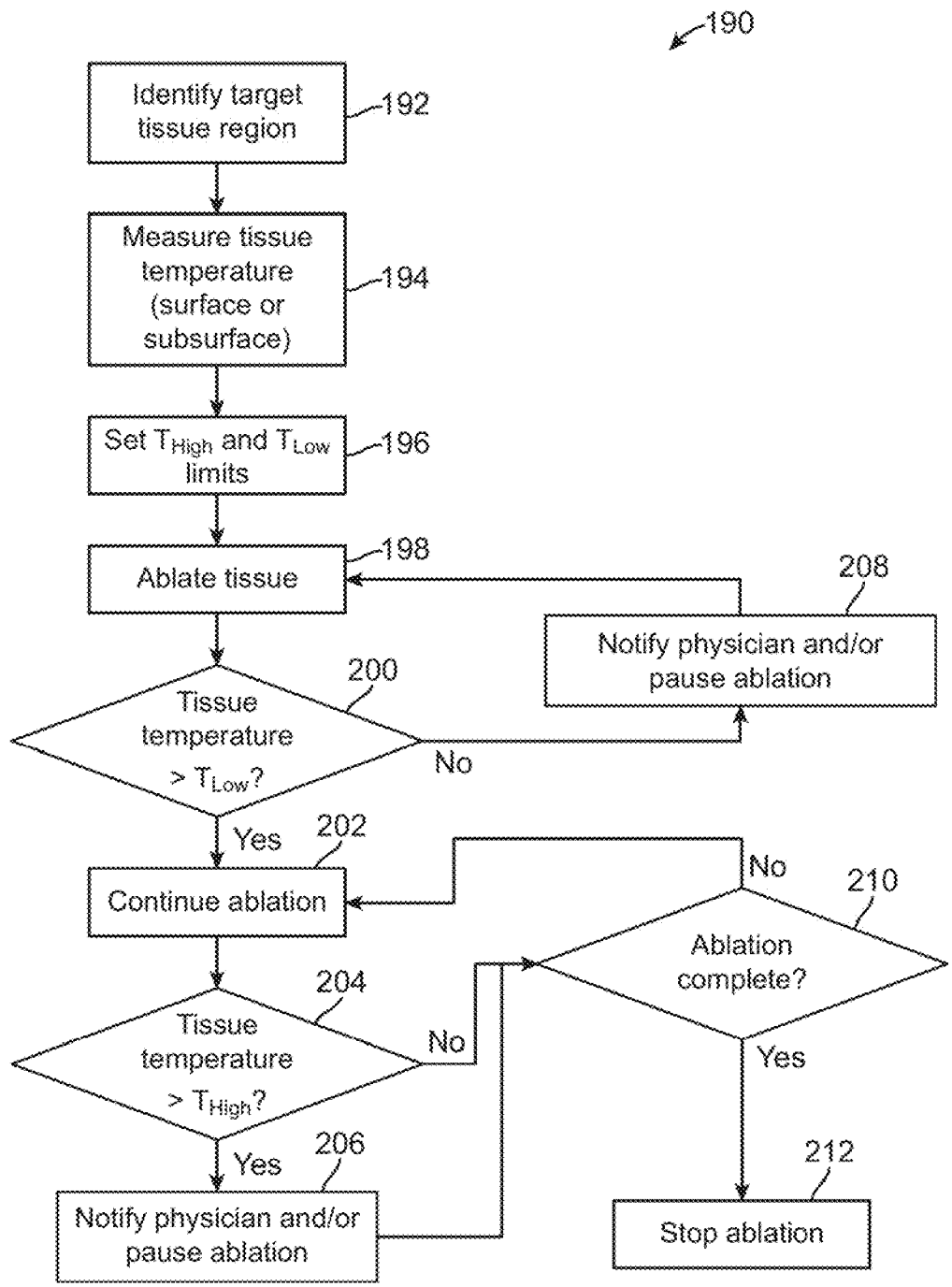
FIG. 10 shows a flowchart illustrating one method for monitoring tissue temperature during ablation treatment.

One example for monitoring tissue temperatures prior to and/or during tissue ablation is illustrated in the flowchart 190 of FIG. 10. Once the targeted tissue region is identified 192 utilizing the devices and methods described above, the tissue temperature (surface and/or subsurface tissue temperatures) may be initially measured 194 utilizing any number of temperature measurement devices. For example, temperature sensors may be positioned along the hood 12 and/or distal membrane of the hood in contact against the tissue surface. Other sensors may include, e.g., thermocouples, thermistors, fluoro-optic temperature sensors, thermochromic markers under direct visualization through the hood 12, etc. Thermochromic markers may be embedded within the distal membrane which may be pressed against the tissue region. Changes in the marker colors which are indicative of the tissue temperature changes may be monitored through hood 12 via the imager or via an automated vision sensing system. Further examples of tissue temperature sensors and methods of their use are described in further detail in U.S. patent application Ser. No. 12/118,439, which is incorporated herein by reference above.

Additionally, needle probes or similar devices may be inserted into the tissue region to be treated to provide a measurement of the sub-surface tissue temperature. Further examples of sub-surface measurement systems and methods of their use which may be utilized with the devices and methods described herein are shown in further detail in U.S. patent application Ser. No. 11/775,837 filed Jul. 10, 2007 (U.S. Pat. Pub. 2008/0009747 A1), which is incorporated herein by reference in its entirety.

With the tissue surface and/or sub-surface temperatures measured, upper $T_{High}$ and/or lower $T_{Low}$ limits for the allowed temperature range are set 196 to ensure adequate power delivery for therapy yet prevent unwanted complications due to excessive (or inadequate) energy delivery. The tissue may then be ablated 198 while the tissue temperature (surface and/or sub-surface) is monitored. So long as the monitored tissue temperature remains above the preset lower $T_{Low}$ temperature limit 200, ablation may continue 202 unabated. In the event that the tissue temperature falls below the lower $T_{Low}$ temperature limit, an audible or visible indicator may notify the user and/or a controller may pause the ablation 208. Attention by the user may allow for adjustment of the ablation treatment and/or preset temperature limits.

During ablation treatment, so long as the upper $T_{High}$ temperature limit is not exceeded 204, ablation may continue until the procedure is completed 210 and ablation treatment may be stopped 212. However, in the event that the monitored tissue temperature exceeds the upper $T_{High}$ temperature limit 204, an audible or visible indicator may notify the user and/or a controller may pause the ablation 206. Attention by the user may allow for adjustment of the ablation treatment and/or preset temperature limits 210 so either allow for continued ablation treatment 202 or cessation of ablation 212.

Aside from or in addition to the different modalities for monitoring tissue parameters, visually assessing the tissue region undergoing ablation may present difficulties in distinguishing between different regions of the tissue due to limitations in the imaging sensors or equipment. One method for improving the visual images of the imaged tissue for assessment by the user may include adjusting the contrast of the captured images. Contrast allows for different tissue regions to be distinguished visually from one another within an image or video. Digital imaging systems such as CMOS image sensors or CCD camera systems have light sensitivities which vary with the wavelength of light. Thus, altering the chromaticity or color of illumination used during imaging could emphasize or de-emphasize certain colors within the imaged field or the change in illumination color composition could target the sensitivity of the image sensor.

Figure 11:
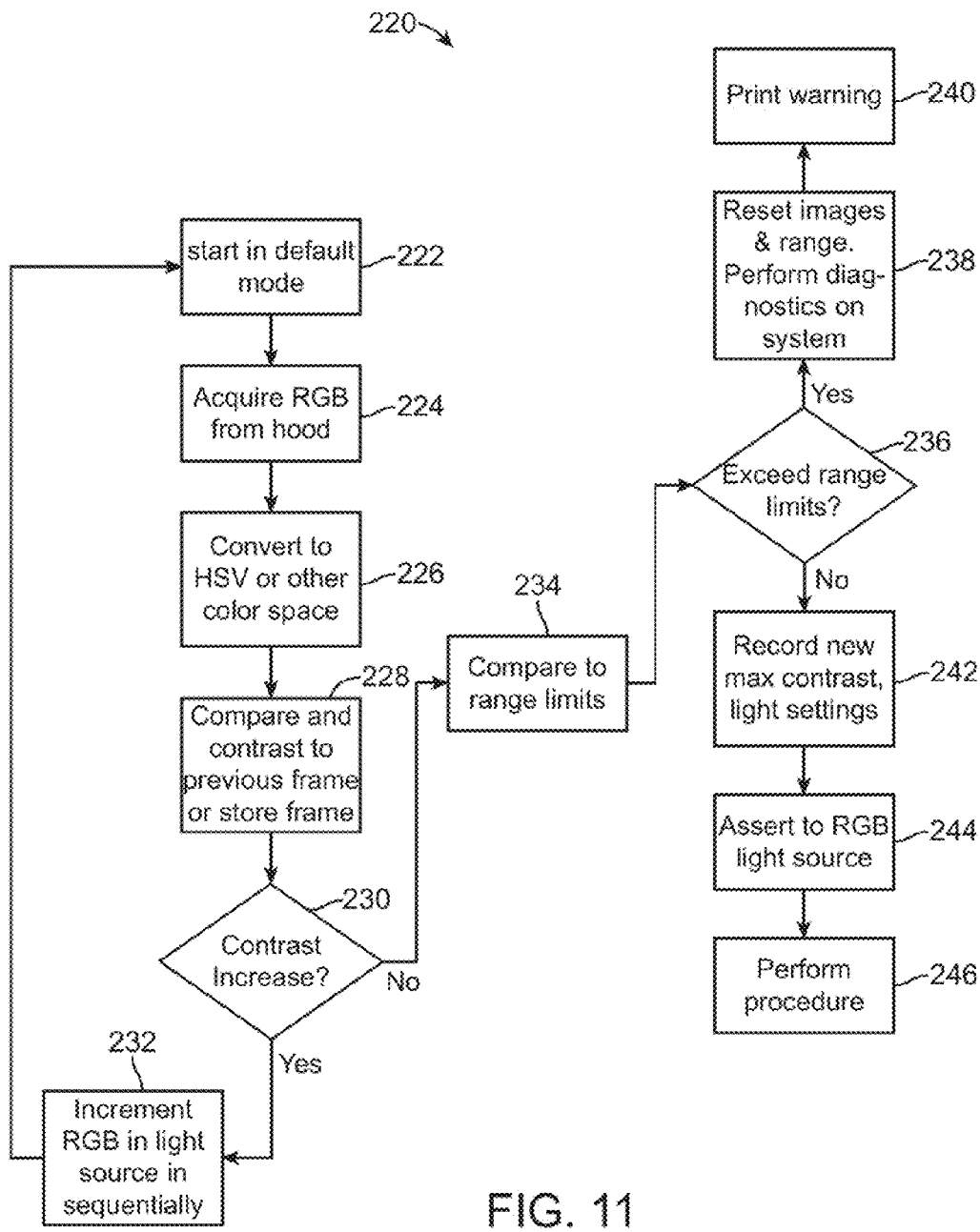
FIG. 11 shows a flowchart illustrating one method for improving a contrast level of visualized tissue to improve the image clarity.

FIG. 11 shows an example for improving image contrast prior to and/or during tissue ablation in flowchart 220. Such a method may be utilized while visually observing tissue ablation through hood 12 via the imager to improve contrast and differentiation between regions of, e.g., normal myocardial tissue and regions where ablation lesions have been created for the treatment of cardiac arrhythmias such as atrial fibrillation. Generally, images acquired from the field of view through hood 12 may have their contrast levels and other relevant characteristics determined and then compared to previously stored data. If additional contrast is needed or desired, a processor may be used to increment various illumination color channels (such as the brightness of different color LED light sources which combine to provide the illumination). Following each incremental adjustment, the processor may re-evaluate the contrast levels and continue to adjust the color balance of the illumination source. If additional changes in contrast are determined to be unnecessary or differences in contrast are nominal or eliminated between comparisons, the processor may evaluate the output image with respect to the range limits of this system.

As shown in flowchart 220, as the images of the tissue region of interest are captured, this may be done while the system begins in a default mode 222. During this image acquisition of the underlying tissue region defined within the field of view of the hood, the RGB (red, green, blue) values of the images may be acquired 224 and determined by a processor and then optionally converted to an HSV (hue, saturation, value) color model (or other color space) 226 to more accurately describe the perceptual color relationships. The newly obtained images with their RGB or HSV values may then be compared and contrasted to a previously obtained frame or stored frame 228 via the processor. In the event that the contrast levels are increased 230 in view of the comparison, the RGB values in the light source illuminating the tissue region may be increased incrementally and sequentially 232 by the processor and the entire process repeated until the contrast levels are equivalent between previously obtained images and newly obtained images 230. Once the contrast levels have been equalized, the RGB or HSV values may be compared against predetermined range limits 234 by the processor.

A comparison of the images against the range limits may yield RGB values which exceed these limits 236, in which case the images and/or range limits may be reset and the processor may perform a diagnostic test on the system 238 and an indication or warning may alert 240 the user. Otherwise, if the images against the range limits yield RGB values which are within the limits, then the contrast levels and light settings may be recorded 242 and the RGB light source may be set to these values 244 and the visualization assessment or procedure may proceed 246.

Figures 12A, 12B:
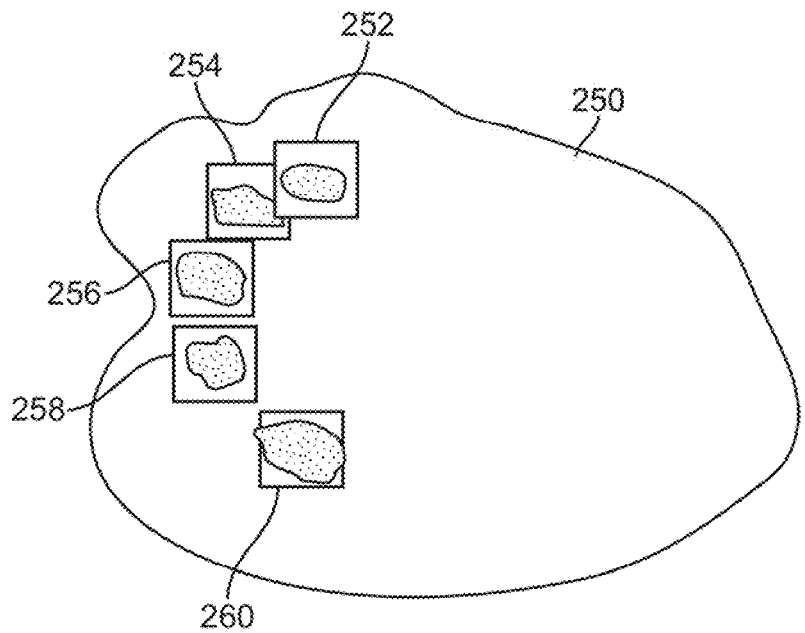
FIGS. 12A and 12B show an illustrative example of a map of lesions created over a tissue region and a generated table of the corresponding parameters for each lesion.

With the imaging contrast levels appropriately adjusted for visualizing the tissue region, visualization and/or treatment of one or more tissue regions may be performed. In the event that multiple lesions are to be formed over a tissue region, each of these lesions may necessitate ablation parameters which vary from one another to optimally treat the tissue region 250 which can vary physiologically depending upon which region is treated. Accordingly, the user may automatically track the parameters and locations which may be unique for each of the lesions formed over tissue region 250, as shown in FIG. 12A. The table in FIG. 12B shows an example of how a processor in communication with the visualization and/or treatment device may catalogue and identify each formed lesion utilizing visual information captured from the field of view through the hood 12.

In one variation, the unique shape of each lesion may be used to determine the "address" of that particular lesion. An edge finding, texture classification, or morphology algorithm may be used to determine the outline, surface pattern, or shape of the lesion from the visual information provided by the visualization device. This information and/or an image depicting the ablation lesion is then constructed into an array and tagged with the appropriate data such as the RF power and the length of time ablation took place to create the particular lesion. Accordingly, first lesion 252 may be identified by its unique shape and/or relative location and its corresponding power level and ablation time may be identified on the array. Likewise, each subsequent lesion, e.g., second lesion 254, third lesion 256, fourth lesion 258, fifth lesion 260, etc. may have its own power level and ablation time associated accordingly.

Alternatively, lesion identification may be accomplished via the usage of color comparison algorithms and/or biological markers on the lesions among other identifiers. This information may be particularly useful for re-identification, comparison and mapping of all lesions on the tissue surface 250. If catheter position information is available, this information may be combined with the data of the array of FIG. 12B to automatically map out the ablation lesions relative to their position within the heart.

Additional control and navigation systems which may be utilized herein are shown and described in further detail in U.S. patent application Ser. No. 11/848,429 filed Aug. 31, 2007 (U.S. Pat. Pub. 2008/0097476 A1) and in Ser. No. 11/848,532 also filed Aug. 31, 2007 (U.S. Pat. Pub. 2009/0054803 A1), each of which is incorporated herein by reference in its entirety.

Figure 13A:
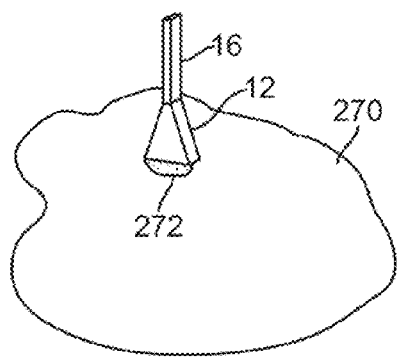
FIGS. 13A and 13B illustrate an example of a first lesion created along a tissue region and the corresponding visual image through the hood and generated map of lesion location.
Figure 13B:
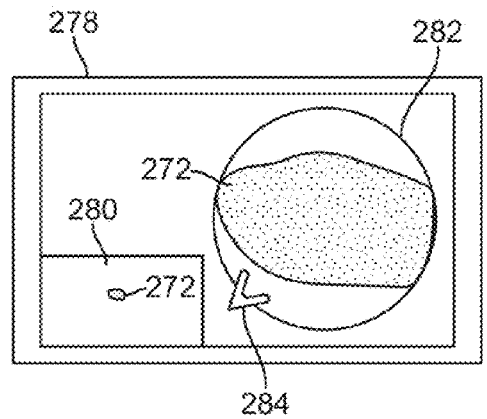

When multiple areas along the tissue region 270 have lesions formed on them, a navigational mini-map may be utilized which allows the physician to view, track and/or map the multiple lesions that are formed on the tissue surface during the ablative treatment. In using the lesion address array previously described, lesions may be detected and/or their relative location to one another may be determined by various methods, such as measuring optical flow as the hood of the catheter moves from one site to another. This information may be then displayed on a map on the monitor 278. For example, a first lesion 272 may be seen on the tissue region 270 in FIG. 13A with the lesion 272 as seen through the hood 12 in the corresponding field of view 282. The location of the first lesion 272 may accordingly be registered and illustrated, e.g., on image 280 of display 278, as shown in FIG. 13B.

Figure 14A:
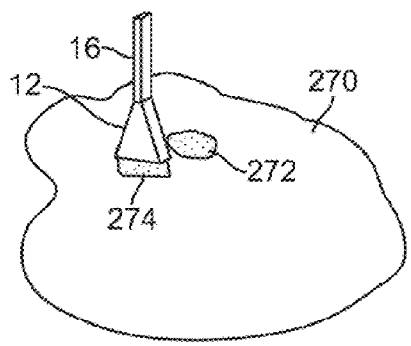
FIGS. 14A and 14B illustrate another example of a second lesion and the corresponding visual image and generated map indicating relative lesion location.
Figure 14B:
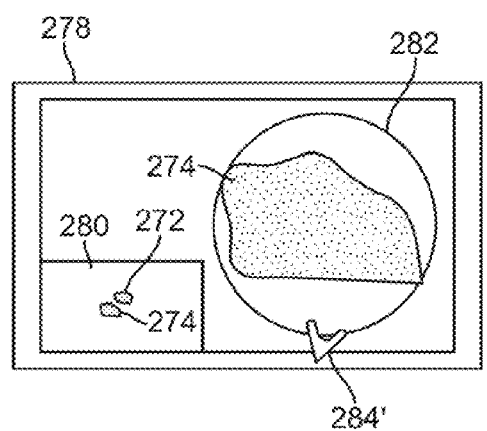
Figure 15A:
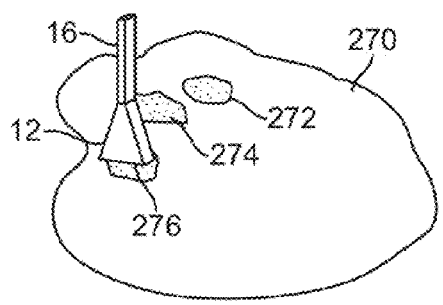
FIGS. 15A and 15B illustrate another example of a third lesion and the corresponding visual image and generated map again indicating relative lesion location.
Figure 15B:
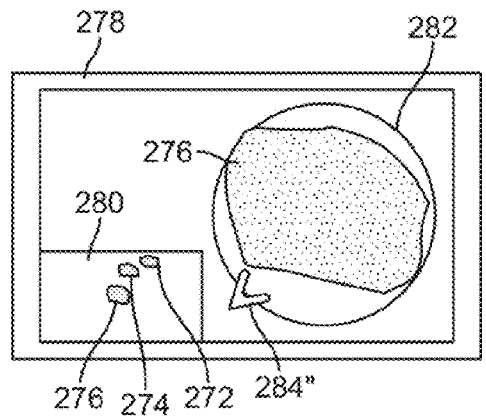

A directional movement indicator may be superimposed to point in a first direction 284 on the monitor 278 to indicate a direction in which the catheter hood 12 is moving (or is to be moved) relative to the tissue surface 270 and/or other lesions. Thus, FIG. 14A shows the position of a second lesion 274 which has been formed (or is to be formed) on the tissue surface 270. Image 280 may illustrate the position of the second lesion 274 relative to the first lesion 272 and the field of view 282 may show the visual image of the lesion 274 itself, as shown in FIG. 14B. The directional indicator may indicate a second direction 284' in which the hood 12 is moving (or is to be moved) to reach the location of the third lesion 276 which is either formed or to be formed. Likewise, FIG. 15A shows the position of a third lesion 276 relative to the first 272 and second 274 lesions while image 280 may reflect the relative positioning on monitor 278. Third lesion 276 may be shown in the field of view 282 while the directional indicator may point to yet another direction 284" in which hood 12 may be moved for lesion visualization and/or formation, as shown in FIG. 15B.

Figure 16:
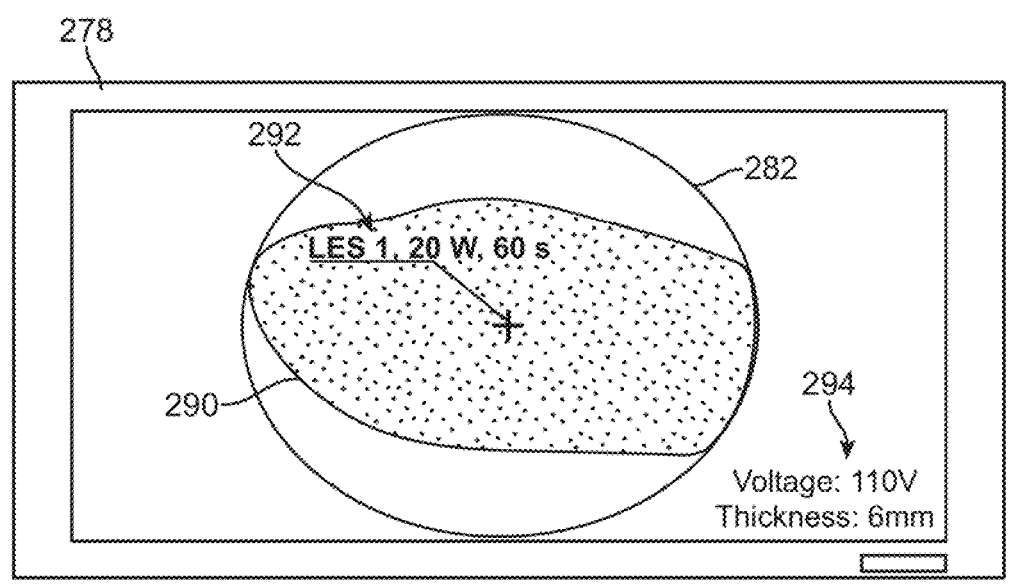
FIG. 16 illustrates a visualized image of tissue with an example of a generated informational overlay imposed upon or in proximity to the visualized image indicating certain parameters, e.g., lesion location, power levels, ablation times, etc.

When providing real-time visual images for the purposes of tissue diagnosis or treatment, it may be useful to overlay relevant information to aid the physician during diagnosis and/or treatment. One such example of an overlay is shown in the monitor 278 of FIG. 16 which illustratively shows the field of view 282 as seen through hood 12 with lesion 290 previously or recently formed. Any number of physiologic or treatment parameters may be overlaid directly upon the monitor 278 for display to the user to facilitate assessment or treatment, e.g., for estimating the depth of the lesion formed. In this example, treatment information 292 (e.g., positional information, applied power levels, time of ablation treatment, etc.) may be superimposed on the image of lesion 290. Any other additional information 294 (e.g., applied voltage, tissue thickness, etc.) may also be displayed upon monitor 278 for display to the user.

Another overlay that may be applied is related to visually representing the electric potential of the tissue surface. Electrodes positioned along the hood may be used to measure the electrical potential (such as the bipolar voltage amplitude or monopolar voltage amplitude relative to a reference catheter or Wilson central terminal) of points on a tissue surface. Further examples of electrodes positioned along the hood and/or distal membrane which may be utilized herein are described in detail in U.S. patent application Ser. No. 12/118,439, which is incorporated herein by reference above.

Figure 17A:
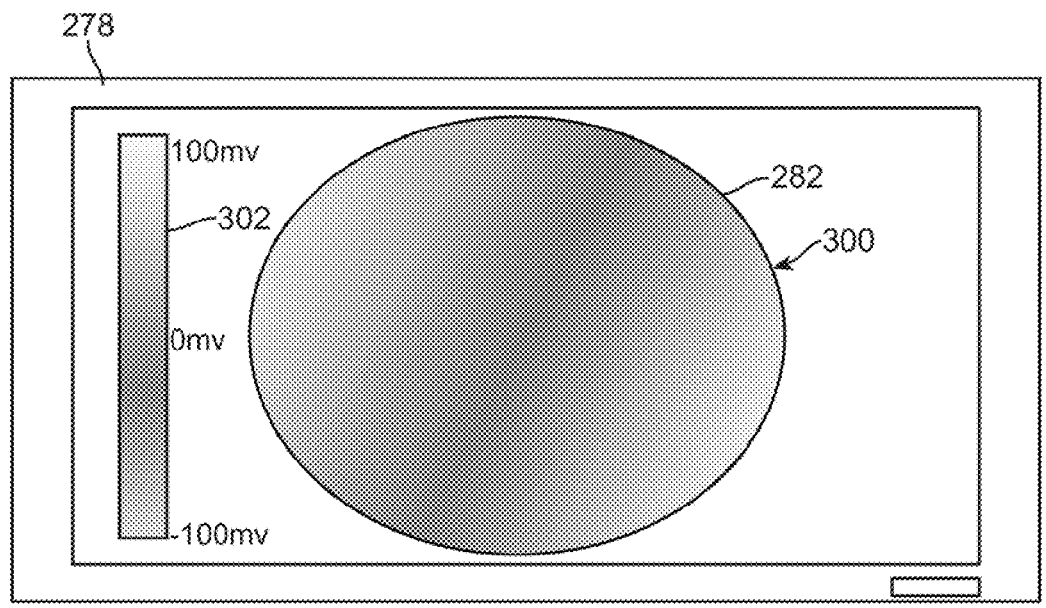
FIGS. 17A and 17B illustrate examples of a visualized region of tissue having its measured electrical potential overlaid upon the image prior to and during or after ablation.
Figure 17B:
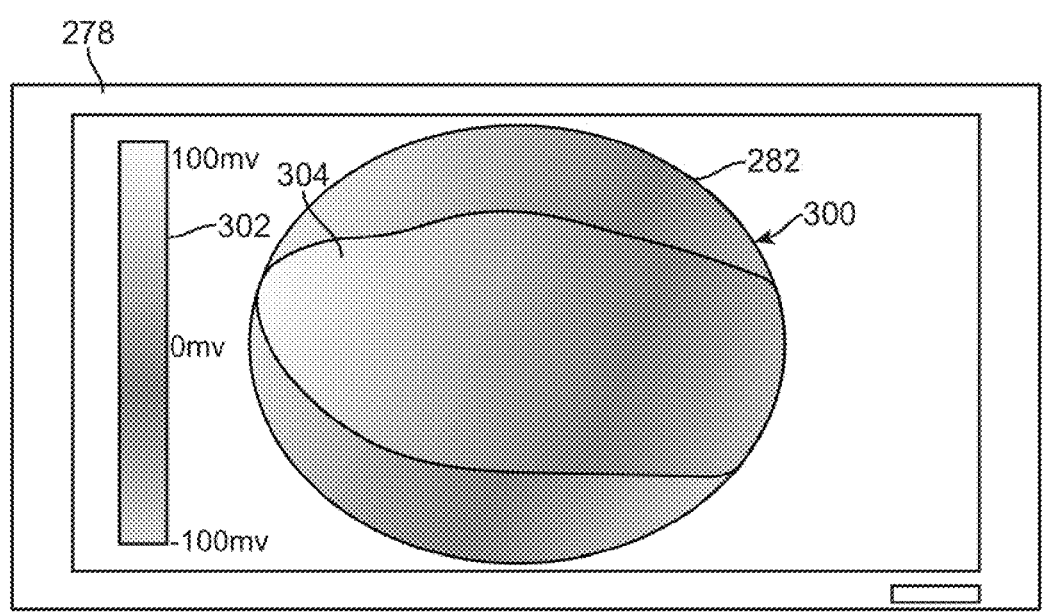

FIG. 17A shows a monitor view of measured gradient of electric potential 300 of the tissue overlaid upon the visualized tissue region seen in the field of view 282 through hood 12. An electrical potential indication chart 302 may be seen also on monitor 278 to indicate the level of detected electrical potential for reference by the user. During lesion formation, as shown in FIG. 17B, the measured electric potential at the region of the lesion 304 may be monitored and overlaid atop the visualized lesion. A threshold value of electrical potential may be optionally preset by the user such that if the measured electrical potential of the lesion is reduced during ablation, e.g., <0.5 mV bipolar voltage, then an indicator may alert the user that the lesion has been successfully electrically isolated from the surrounding tissue. This may facilitate physician assessment as to when lesion formation is complete.

Figure 18A:
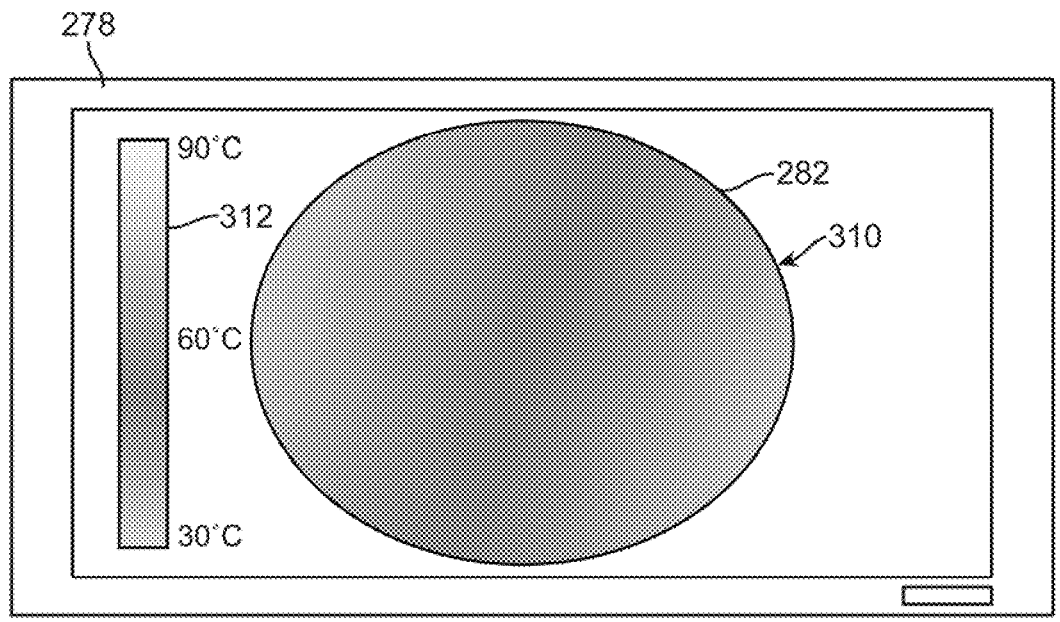
FIGS. 18A and 18B illustrate examples of a visualized region of tissue having its measured temperature overlaid upon the image prior to and during or after ablation.
Figure 18B:
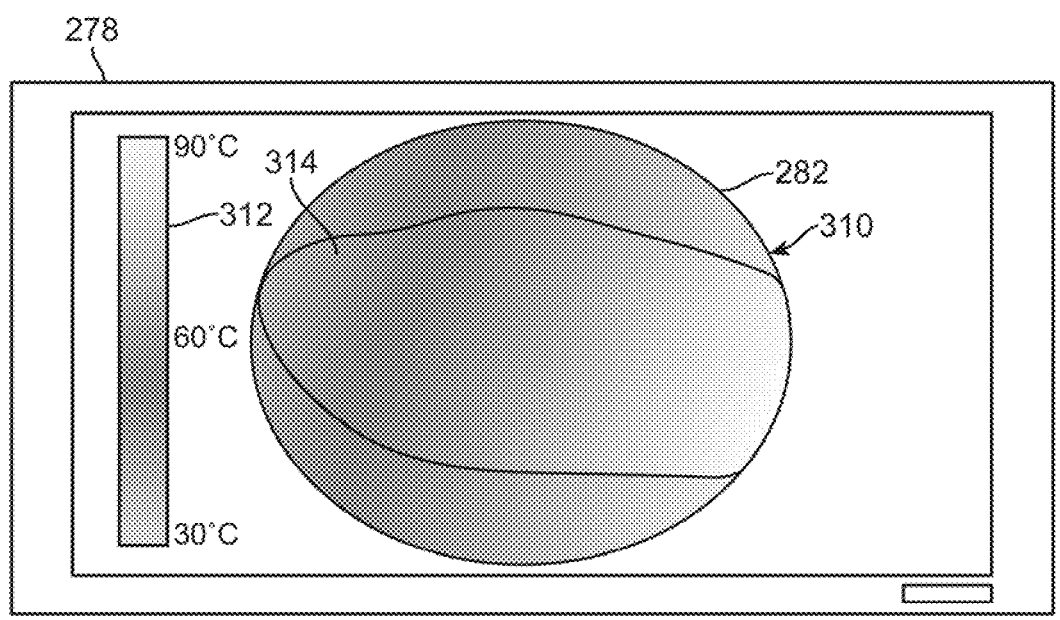

Additionally and/or alternatively, other information may be overlaid upon monitor 278 for facilitate physician assessment. For example, FIG. 18A illustrates an example where the temperature gradient 310 of the visualized tissue may be measured and superimposed upon the visualized tissue utilizing temperature sensors, as described in further detail in U.S. patent application Ser. No. 12/118,439, which is incorporated herein by reference above. A temperature indication chart 312 may be shown along the monitor 278 for reference by the user. As previously described, ablation may be controlled such that the tissue remains within prescribed temperature limits. Overlaying the temperature information of the lesion 314 as it is being formed may assist the physician, e.g., in assessing whether to terminate the ablation should a localized hot spot develop on the tissue surface, as shown in FIG. 18B.

Figure 19:
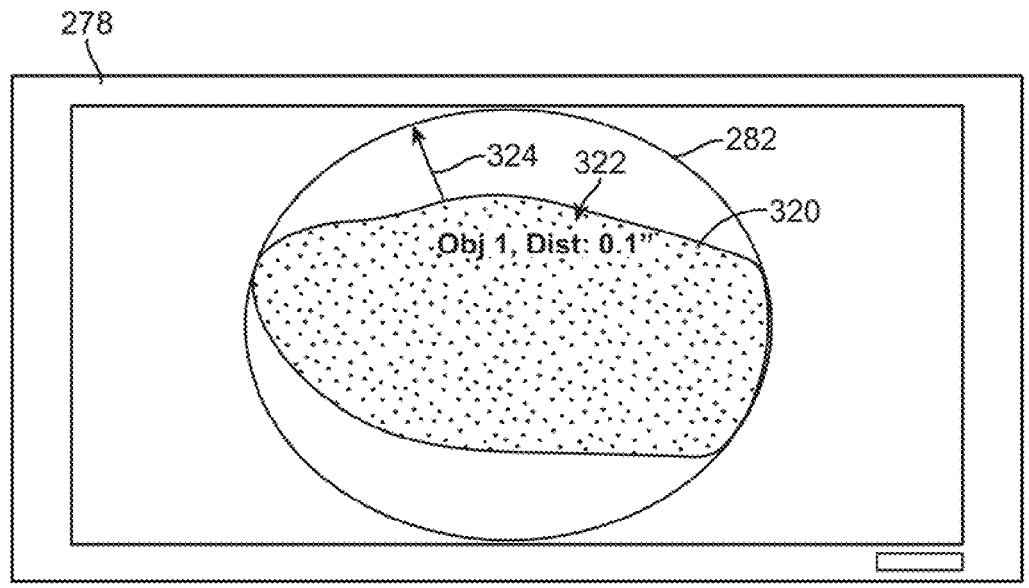
FIG. 19 shows an example of a visualized image of region with specified informational data, such as distance from a lesion to a specified anatomical feature, overlaid upon the image.

Yet another example of an informational overlay which may facilitate tissue treatment assessment may incorporate the distance of a tissue region to be treated (or undergoing treatment) to a predetermined anatomical object or location. For example, ablation of heart tissue typically occurs near the location of the esophagus, which lies very close to and often touches the outer wall of the left atrium, within the body. The heat from the ablation procedure may penetrate through the tissue of the left atrium and reach the esophagus. Uncontrolled ablation may thus present a risk as lesions may be formed which extend towards or in proximity to the esophagus thus potentially damaging the esophageal tissue. Such damage is extremely dangerous as the damaged esophagus may become infected and lead to an esophageal fistula (hole in the esophagus). Over time, this may lead to an infection spreading into the heart wall which carries a relatively high mortality rate. To avoid damage to the esophagus (or any other object or anatomical structure in proximity to the ablated tissue region), mapping catheters and other imaging methods such as use of swallowed contrast agents or probes to indicate either the pre-operative or real-time position of the esophagus may be used. To that end, some physicians have used standard mapping catheters to record the pre-procedure location of the esophagus. However, such a pre-procedure location determination fails to account for the mobile nature of the esophagus. The esophagus generally does not remain stationary. Rather, the esophagus often moves back and forth thereby positioning itself in different locations relative to the heart wall. As such, the esophagus may change its location during a catheter-based endocardial procedure. The pre-procedure determination fails to account for this movement. Accordingly, displaying information in real-time such as the proximity of the ablation catheter to the probe on the monitor 278 may facilitate such treatments, as shown in FIG. 19, which shows lesion 320 and distance information to a preselected object 322, such as the esophagus. Moreover, a directional indicator to the object 324 may also be imposed on monitor 278 to indicate to the user the relative direction to the object.

Non-limiting examples of suitable analysis techniques for determining distance for use with the system, devices, and methods described herein may include impedance measurement, pacing signal amplitude measurement, use of magnetic fields, use of Hall effect sensors, inductance measurement, capacitance measurement, etc. Thus, a physician may continuously monitor throughout an entire mapping and/or ablation procedure the position of the object, such as the esophagus, relative to the device in use in the heart. This continuous, real time monitoring of the location of the esophagus may further accounts for the movement of the esophagus to decrease the risk of damage to the esophagus. Additional examples which may be utilized herein are further described in detail in U.S. Pat. Pub. 2007/0106287 A1, which is incorporated herein by reference in its entirety.

Figure 20:
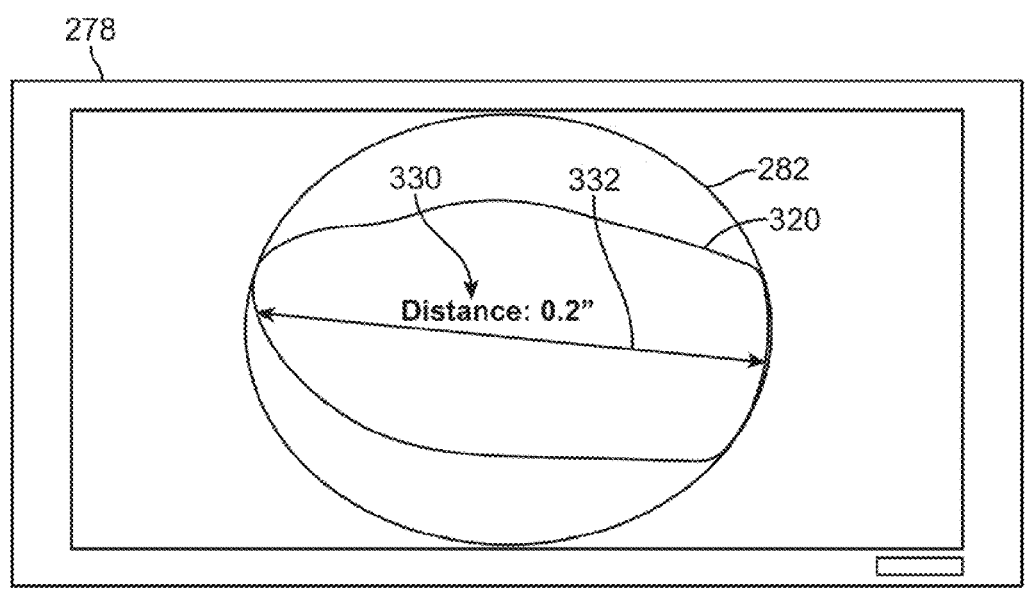
FIG. 20 shows an example of a visualized region of tissue with specified information data, such as lesion length, overlaid upon the image.

It is also possible to overlay information relating to particular metrics on the monitor 278 during visualization or ablation. For example, FIG. 20 illustrates an example of how distances 332 between two selected points may be measured directly on the monitor 278 to provide metric information 330 such as the length of a particular lesion. Such overlays may be utilized to determine, e.g., the surface size of the lesion precisely to facilitate physician assessment of lesion size. It may also be used to accurately measure anatomical features in the body. Typically, a reticule of a known distance may be included within the field of view which would allow for calibration of the measurement to a know distance. The accuracy of this measurement would be highest for objects that are in the same plane as the calibration distance. Further examples of measuring tissue regions in vivo which may be used herein with the devices and methods are shown and described in detail in U.S. Ser. No. 12/118,439 filed May 9, 2008, which is incorporated herein by reference in its entirety.

Aside from measuring anatomical features, another feature which physicians may utilize with the captured visual images of tissue may also include the monitoring of changes in color of a lesion formed over time. Tissue color may be used as a good indicator of the stage of completion of the lesion forming process as normal, unablated myocardial tissue is characteristically pink or red in color. During ablation the lesion site will change color due to heating, dessication, denaturation of proteins, and/or ischemia. The lesion site will typically become white and then possibly black, brown, or yellow as ablation continues if applied beyond the usual limits. During real-time visualization and ablation it may become difficult to distinguish the degree of color change that has taken place due to the graduated nature of the color change.

Figure 21A:
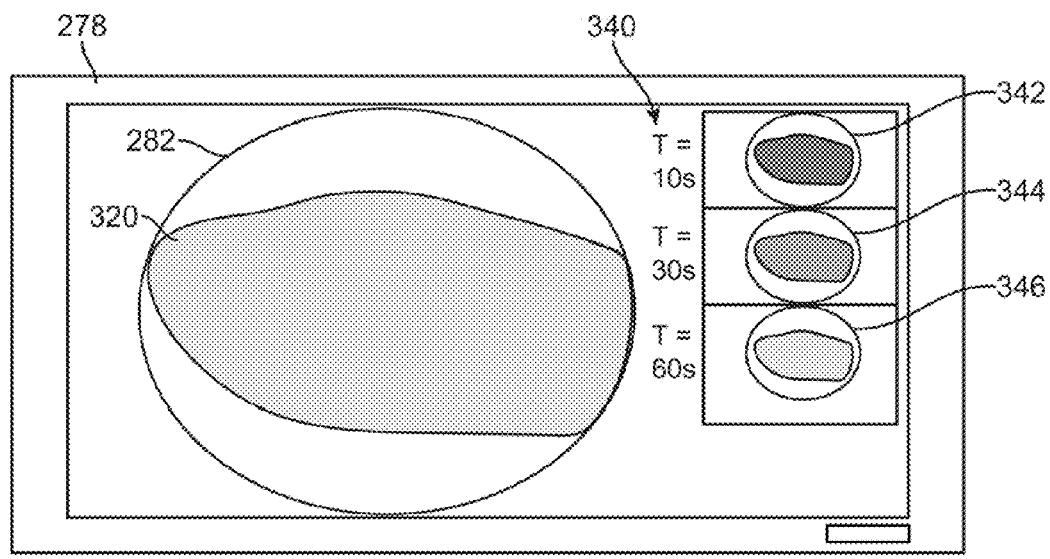
FIGS. 21A and 21B show examples of a visualized region of tissue which is treated or has been treated by formation of a lesion while images the same region is captured during the ablation process for comparison.

An example of monitoring color changes in tissue during ablation treatment is illustrated in FIG. 21A, which shows an overlay of multiple images of the tissue surface at preselected time intervals as ablation progresses from, e.g., 10 secs to 60 secs. The time intervals at which the captured images may be selected for viewing may be selected at relatively higher or lower sampling rates. As shown in this example, images of lesion 320 may be captured, e.g., at a recorded ablation time 340 of 10 sec, 30 sec, and 60 sec with a first corresponding image 342, second corresponding image 344, and third corresponding image 346 showing the progression of the tissue coloring from a pink or red state eventually to a blanched condition. Having these images simultaneously displayed may provide contextual information to the user in determining whether sufficient ablation had occurred in the tissue being treated.

Figure 21B:
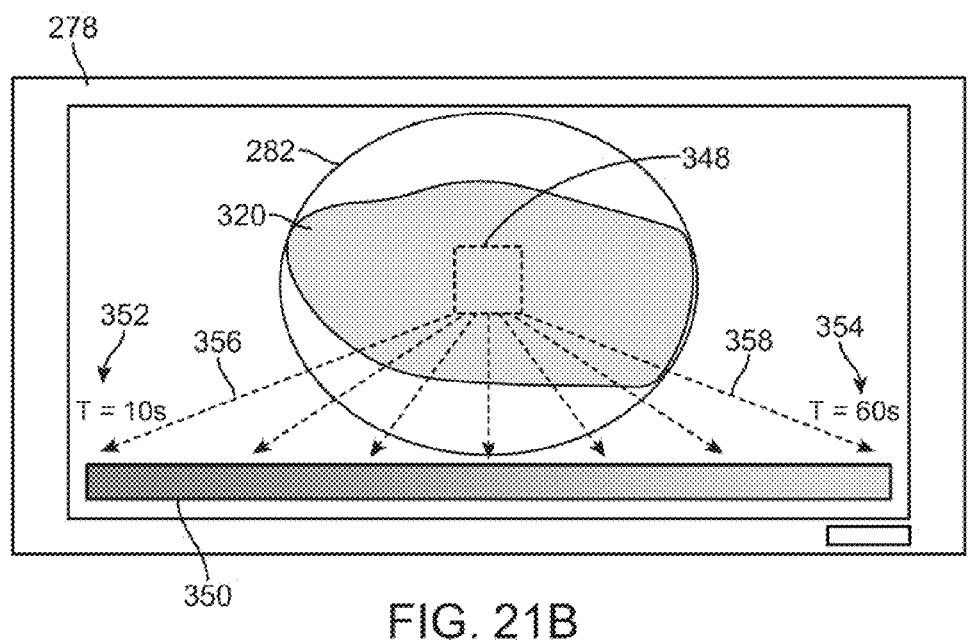

Another variation is shown in FIG. 21B which illustrates monitor 278 showing a particular measured region 348 of lesion 320 tracked and imaged over a period of time from a first measured ablation time 352 to a final measured ablation time 354, e.g., from 10 sec to 60 sec. A temperature chart 350 may be provided illustrating the eventual change in tissue color as ablation progresses through the ablation treatment. One or more indicators may show the tissue coloring at a corresponding ablation time, e.g., from a first corresponding tissue image 356 to a final corresponding tissue image 358, which may be available to the user for assessment.

Figure 22:
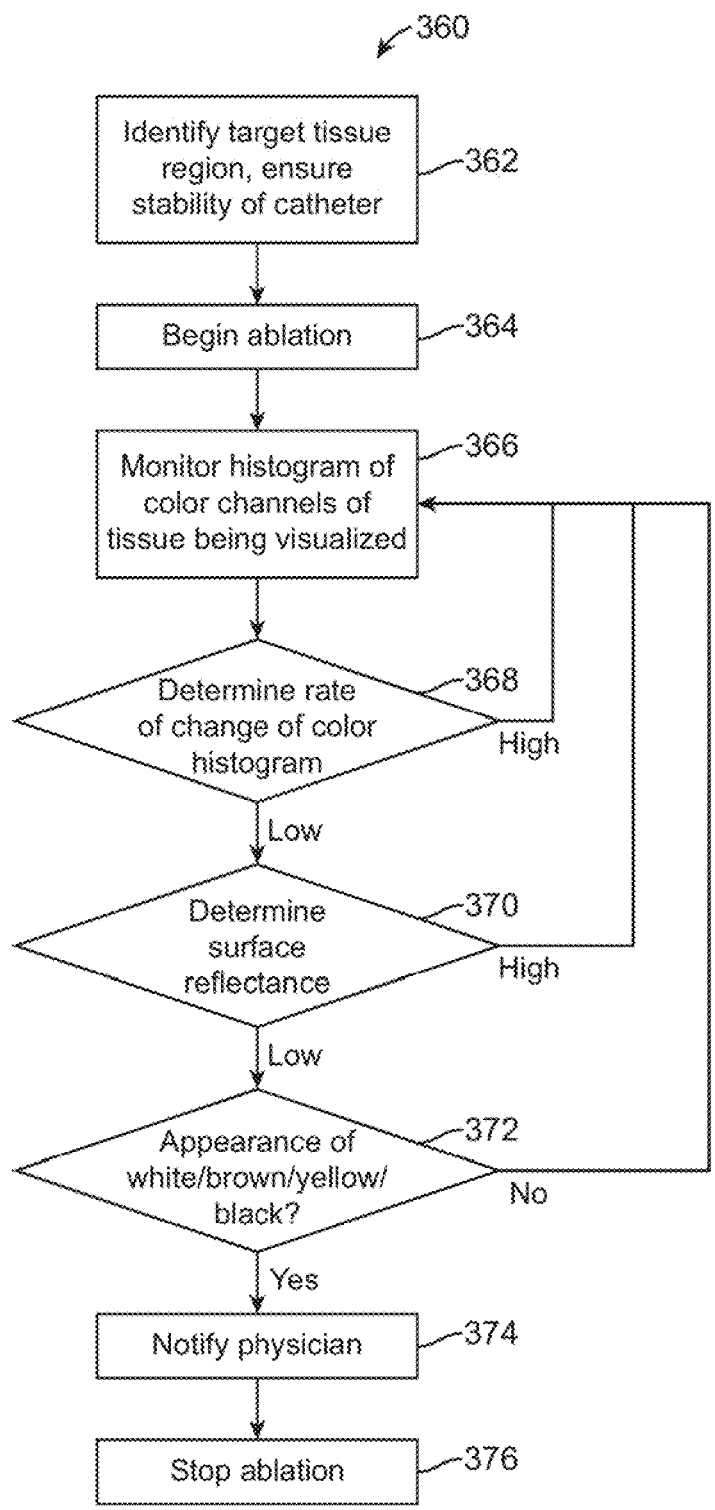
FIG. 22 shows an example for visually monitoring a degree of blanching of a tissue region undergoing ablation treatment.

In monitoring the blanching of the tissue being treated during ablation, the degree of blanching may be determined by a number of different methods. Blanching occurs as a result of heating a tissue region which causes proteins to denature and desiccate. This eliminates blood flow from the tissue hence turning it from a pink or red color to a white color. Thus, blanching of tissue may serve as a visual indicator of ablated tissue. One example is shown in the flowchart 360 of FIG. 22 which illustrates how certain tissue characteristics may be monitored. Once the target tissue to be treated has been identified and the visualization and treatment catheter securely apposed against the tissue surface 362, ablation may be initiated 364 while under direct visualization through hood 12. A processor in communication with the imager may monitor a histogram of color channels of the tissue being visualized 366 and the processor may then determine a rate of change of the color histogram 368. If the rate of change is determined by the processor to be higher than a preset limit, this may be an indication that the tissue is blanching at a higher rate than desired and the processor may continue to monitor the tissue color change. Otherwise, if the rate of color change is lower than the preset limit, then the processor may determine the degree of surface reflectance 370. Again; if the processor indicates that the surface reflectance is higher than a preset value, then the color may continue to be monitored otherwise if the reflectance is lower than the preset value, a determination may be made as to whether there is any appearance of particular colors from the tissue which may indicate that ablation of the tissue is nearing completion, e.g., white, brown, yellow, black, etc. 372. If the processor does detect the appearance of any of these particular colors, an audible or visual indicator may notify the physician 374 and ablation may be stopped automatically by the processor or directly by the physician 376.

Figure 23:
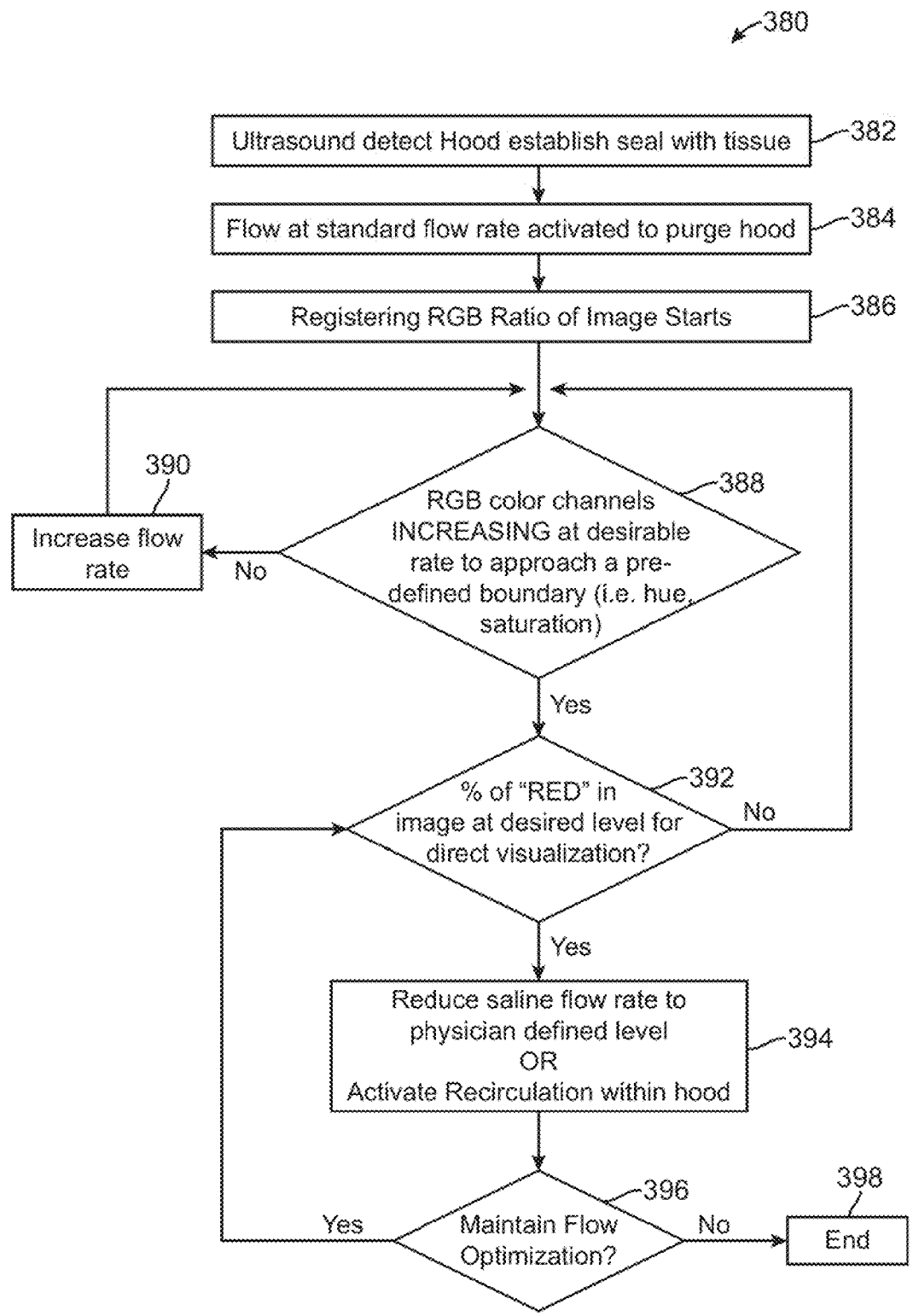
FIG. 23 shows an example for monitoring and/or controlling a flow of saline before and/or during ablation treatment.

Additionally and/or alternatively, a processor may control the flow of the purging fluid which may also be used to conduct a current to the tissue to be treated. As illustrated in FIG. 23, flowchart 380 shows an example where the color change of the lesion may also be utilized for controlling or altering the purging fluid flow through the hood and over the tissue region being visualized and/or treated. It is generally desirable to deliver the lowest amount of saline to the patient through the hood 12 as an excessive flow of saline may cause the balance of electrolytes in the body to fluctuate potentially resulting in hyponatremia. Thus, once the hood 12 has been sufficiently apposed against the tissue surface, e.g., by utilizing ultrasound 382 as described above or through other methods, the saline fluid may be introduced into hood 12 to begin purging of the blood within the hood and to clear the visualization field 384. This fluid may be introduced at an initial predetermined rate and registering of the RGB ratio of the imaged underlying tissue may begin 386, as described above.

If the processor determines that the detected RGB color channels are increasing at a desirable preset rate in approaching a predefined boundary (utilizing parameters such as hue, saturation, etc.) 388, then the percentage of the color red may be determined for the captured image 392 and if the this percentage is above a predetermined level, then this is an indication that the visual field is sufficiently clearing of blood. However, if the RGB color channels are determined not to be increasing at a desirable rate, then the processor may automatically increase a flow rate 390 of the saline into the hood 12 to increase the rate at which blood is cleared. Likewise, if the percentage of the detected color red is found to be below the predetermined level, then monitoring of the color may be continued until the blood is sufficiently cleared from the visual field of hood 12.

Once the percentage of the detected color red is at a desired level, then the saline flow rate may be reduced to a predetermined level 394, e.g., defined by the physician or active recirculation of the saline may be produced within the hood. A determination may then be made as to whether to maintain the flow optimization 396 in which case if flow optimization is continued, then the color change within the hood may be continued to be monitored. Otherwise, the flow control may be terminated 398.

Figure 24:
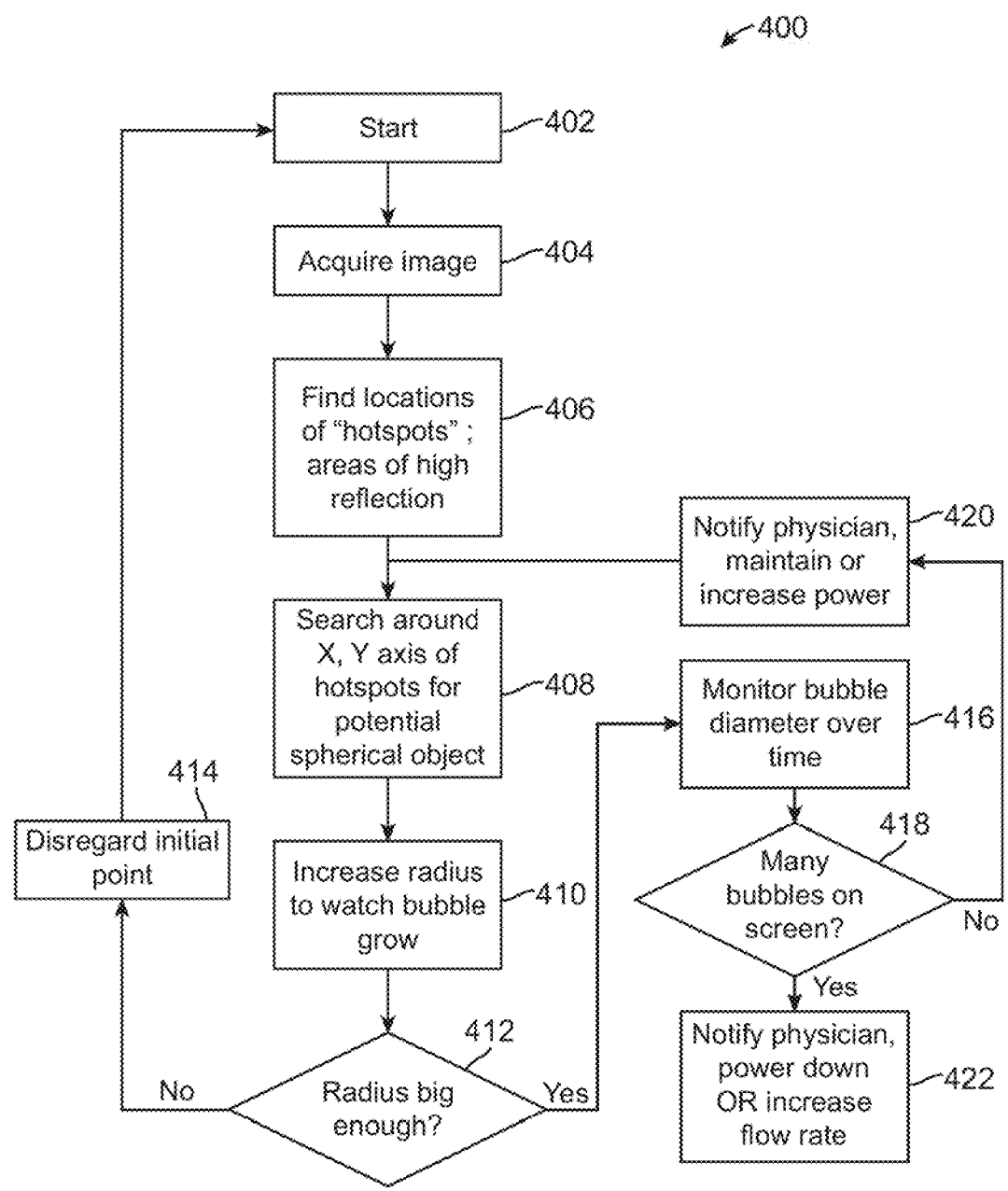
FIG. 24 shows an example for visually monitoring bubble formation on tissue during ablation.

Yet another parameter utilizing the captured visual images during tissue ablation may include the detection of bubbles during ablation. The formation of bubbles may be visible on the monitor near or at the edges of the visual field and these bubbles may be generally indicative of high rates of heating, over-blanching of tissue, or a potential steam popping. FIG. 24 illustrates a flowchart 400 which shows one method for utilizing bubble detection where the process may begin 402 by acquiring the visual image 404, as previously described. The visual image may be processed by a processor to find locations of any "hotspots" 406, i.e., areas of high reflection, which may be indicative of the presence of bubbles. The visual field may then be searched for potentially spherical objects 408 and further monitored to determine whether a radius or diameter of any spherical objects are growing 410 during the ablation process. In the event that the detected radius is not any larger than a preset limit 412, then the process of searching may continue 414. Otherwise, if the radius is determined to exceed the preset limit, then the bubble diameter may continue to be monitored over time 416. The processor may then determine whether the number of detected bubbles in the visual field exceed a threshold value 418. In the event that the number of detected bubbles are insufficient, the physician may be notified and/or the power level may be maintained or increased 420 and the visual field may be continued to be monitored for the formation of bubbles. Otherwise, if the number of detected bubbles exceed the threshold number, then an alert may notify the physician and/or the system may power down automatically and/or the flow rate may be increased to cool the tissue region down in temperature 422.

The system then alerts the physician to take a measure of corrective actions which may include increasing the saline flow rate or powering down the system among other things. Bubbles may be difficult to detect with the naked eye, hence this protocol may be useful in alerting physicians immediately upon the presence of even tiny bubbles.

Additional methods and systems for bubble detection during tissue treatment are further described in detail in U.S. patent application Ser. No. 12/118,439 filed May 9, 2008, which has been incorporated herein by reference above.

The various protocols or methods disclosed may be used in any combination for processing the visual images generated. Additionally the overlays disclosed may be used in any combination as well to provide users with one or more layers of information.

Figure 25A:
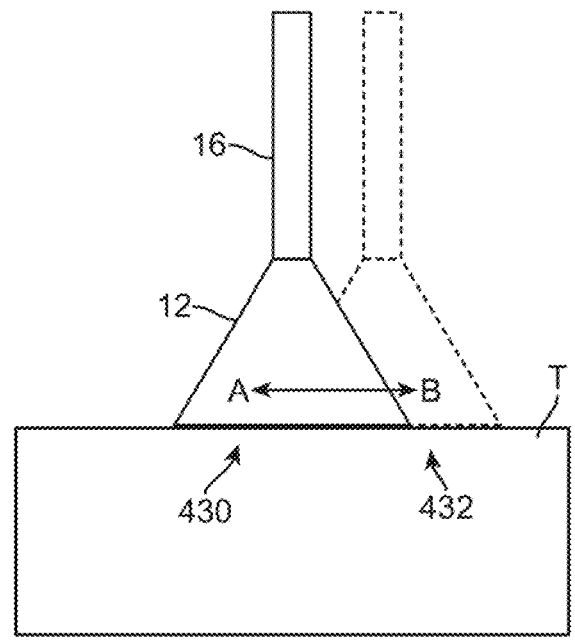
FIGS. 25A and 25B illustrate an example of inadvertent hood movement over a tissue region and the resulting change in the visual field.
Figure 25B:
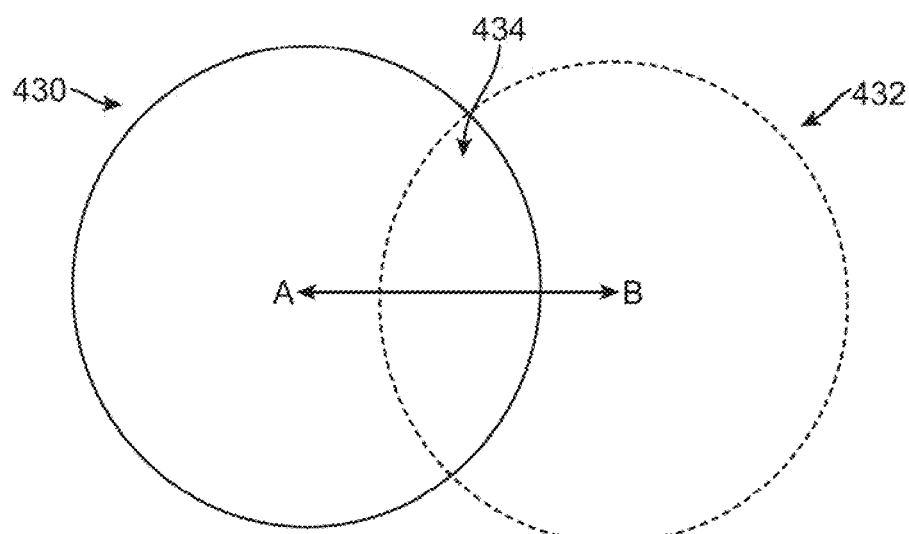

In yet another example for processing captured visual images of tissue regions, FIGS. 25A and 25B illustrate side and plan views of a hood 12 which is placed into contact against a tissue region T to be visualized and/or treated. As the underlying tissue region moves such as during a cardiac or respiratory cycle, hood 12 may be inadvertently shifted from a first location 430 to a second location 432 over the tissue surface, as indicated respectively by two points labeled A and B. When such movement occurs, the region being visualized may move continually making it difficult to observe the tissue or to perform any procedures upon the tissue. Such movement can be monitored visually by several methods such that the user is able to determine an appropriate time to begin a procedure. The overlap region 434 may be calculated between the first location 430 and second location 432 compared against a threshold limit. With the distance of hood movement known, a procedure may be initiated and/or stopped appropriate each time the hood 12 is expected to move such that treatment may be synchronized according to hood and tissue movement.

Figure 26A:
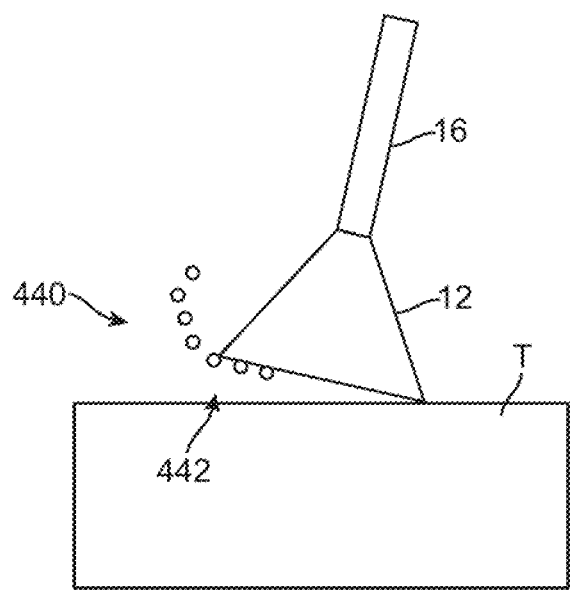
FIGS. 26A and 26B illustrate an example of incomplete hood apposition against the tissue surface and the resulting formation of bubbles along one side of the visual field.
Figure 26B:
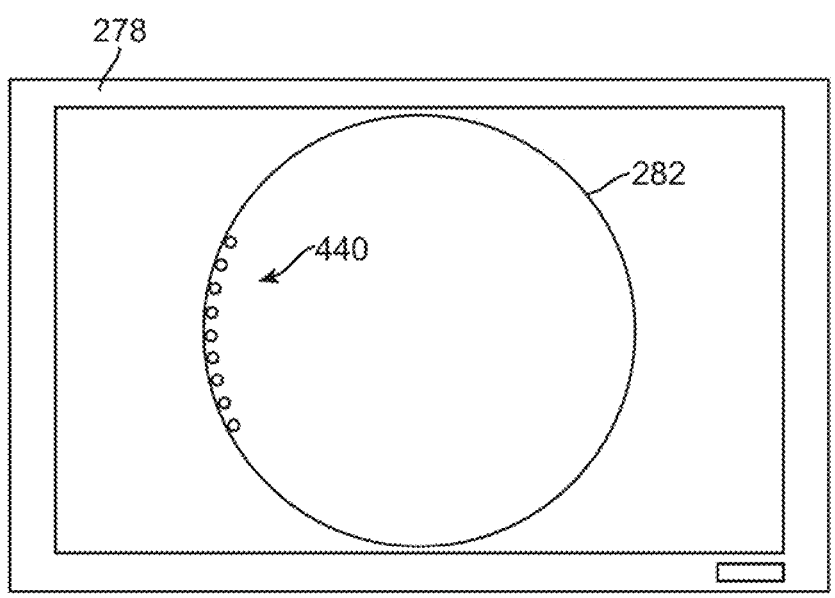

In yet another example of utilizing the captured images, FIGS. 26A and 26B show side and monitor views of a hood 12 which is insufficiently apposed against the surface of a tissue region T to be visualized and/or treated. As it may be difficult to determine if the hood 12 is seated perpendicularly on the tissue surface or is in an off-axis configuration, it may be possible to detect and correct for such off-axis alignment from the tissue by processing of the visual images. If hood 12 is not placed into direct apposition against the tissue surface, gases introduced into hood 12 along with the purging fluid may form along the side of hood 12 which is not in contact with the tissue, i.e., bubbles 440 may form along a gap or spacing 442 between hood 12 and the tissue surface. These bubbles 440 may be visible in the field of view 282 and thus alert the user that the hood 12 positioning along the tissue may require readjustment.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of imaging a tissue region which is under motion, comprising:
   visualizing the tissue region within a body via an intravascular imaging catheter by viewing the tissue region through an open hood in contact with the tissue region and where the hood is purged of blood with a fluid, the visualizing resulting in a plurality of visual images of the tissue region;
   recording electrical activity of the tissue region while visualizing the tissue region, the recording performed with a computer;
   receiving a selection of a recurring portion of an event which repeats at least periodically in the electrical activity, the receiving performed with the computer;
   selecting a visual image from the plurality of visual images of the tissue region captured by the intravascular imaging catheter during an instance of the recurring portion of the event, the visual image corresponding to the recurring portion of the event, the selecting performed with the computer;
   capturing one or more additional visual images gated by the event over a period of time;
   registering the selected visual image with one or more ablation parameters associated with an ablation process performed on the tissue region, the registering performed with the computer; and
   displaying the selected visual image with the one or more registered ablation parameters, the displaying performed with the computer.

2. The method of claim 1 further comprising displaying the visual image corresponding to the event.

3. The method of claim 1 further comprising selecting a plurality of visual images each captured during the event over a plurality of repeated events.

4. The method of claim 1, wherein the visualizing comprises visualizing cardiac tissue within a chamber of a heart.

5. The method of claim 1, wherein the visualizing further comprises recording the visual images of the tissue region simultaneously while recording the electrical activity.

6. The method of claim 1, wherein the recording comprises recording electrocardiogram data of the tissue region.

7. The method of claim 1, wherein the selecting an event comprises selecting an electrical event during a QRS Complex of the tissue region.

8. The method of claim 1 wherein the one or more ablation parameters is an operational parameter of an ablation catheter and is selected based upon a detected thickness of the tissue.

* * * * *